United States Patent

Strunk et al.

[11] Patent Number: 5,169,430
[45] Date of Patent: Dec. 8, 1992

[54] BENZENESULFONAMIDE DERIVATIVES AND METHODS FOR THEIR PRODUCTION

[75] Inventors: Richard J. Strunk; Allyn R. Bell, both of Cheshire, Conn.

[73] Assignee: Uniroyal Chemical Company, Inc., Middlebury, Conn.

[21] Appl. No.: 742,957

[22] Filed: Aug. 9, 1991

[51] Int. Cl.5 .............. A01N 43/48; C07D 413/00; C07D 211/72; C07D 211/84
[52] U.S. Cl. ........................... 71/92; 71/88; 544/123; 544/309; 544/310; 544/311; 544/312; 544/313; 544/314
[58] Field of Search ............... 544/309-314, 544/123; 71/92, 88

[56] References Cited

U.S. PATENT DOCUMENTS

| | | | |
|---|---|---|---|
| 4,859,229 | 8/1989 | Wenger et al. | 71/92 |
| 4,941,909 | 7/1990 | Wenger et al. | 71/92 |
| 5,017,211 | 5/1991 | Wenger et al. | 71/92 |
| 5,041,156 | 8/1991 | Suchy et al. | 71/92 |
| 5,055,551 | 10/1991 | Schmidt et al. | 528/380 |
| 5,061,618 | 10/1991 | Parton et al. | 430/584 |
| 5,068,393 | 11/1991 | Maignan et al. | 560/51 |

OTHER PUBLICATIONS

J. Heterocyclic Chemistry, (1972), 9(3), 513-22.

Primary Examiner—Cecilia Tsang
Attorney, Agent, or Firm—Glenn E. Karta

[57] ABSTRACT

A compound having the structural formula

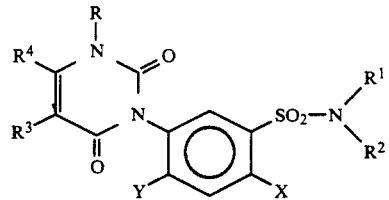

wherein:
R is hydrogen, $C_1-C_4$ alkyl, $C_1-C_4$ haloalkyl, formyl, $C_2-C_6$ alkanoyl, $C_3-C_4$ alkenyl or $C_3-C_4$ alkynyl, or alkali metal;
X is $C_1-C_4$ alkyl, $C_1-C_8$ alkoxy, cyano, or halogen;
Y is hydrogen, halogen, or $C_1-C_4$ dialkylamino;
$R^1$ is hydrogen, $C_1-C_8$ straight chain or branched alkyl, $C_3-C_8$ cycloalkyl, $C_3-C_8$ alkenyl, $C_3-C_8$ alkoxy or $C_3-C_8$ hydroxyalkyl;
$R^2$ is hydrogen, $C_1-C_8$ straight chain or branched alkyl, $C_3-C_8$ alkenyl, $C_3-C_8$ cycloalkyl, halo substituted $C_3-C_8$ alkenyl, $C_3-C_8$ alkynyl, $C_1-C_4$ alkoxy, hydroxy $C_1-C_4$ alkyl, cyano $C_1-C_4$ alkyl, 2,3-epoxypropyl, 2,2-dialkoxyethyl, alkoxyalkyl, phenyl, aralkyl, $C_1-C_4$ acyl, $C_1-C_4$ carbalkoxyalkyl, $C_1-C_4$ carbalkoxyalkyl substituted by $C_1-C_4$ alkyl, phenylmethyl or methylthioethyl, (1,3-dioxolan-2-yl)alkyl, dialkylaminoethyl, or tetrahydrofuranylmethyl;
$R^3$ is hydrogen, halogen or $C_1-C_4$ alkyl;
$R^4$ is $C_1-C_4$ alkyl or $C_1-C_4$ haloalkyl;
$R^1$ and $R^2$ taken together form a $C_3-C_8$ membered heterocyclic ring containing one or more heteroatoms.

In addition, processes and novel intermediate compounds that are useful for making the compound are set forth. A method for controlling weeds which comprises applying a herbicidally effective amount of the compound recited above is described. Also disclosed is a composition useful as an herbicide which includes a compound of this invention and a suitable carrier therefor.

12 Claims, No Drawings

BENZENESULFONAMIDE DERIVATIVES AND METHODS FOR THEIR PRODUCTION

FIELD OF THE INVENTION

This invention relates to a class of compounds, i.e., benzenesulfonamide derivatives, having substituted thereon a pyrimidinyl moiety, which compounds exhibit desirable pre- and post-emergent herbicidal activity. In other aspects, this invention relates to herbicidal compositions incorporating such compounds and to a method of controlling the growth of undesirable plants, such as weeds. In further aspects, this invention relates to novel intermediates useful for the production of the novel herbicides and to processes for producing such compounds.

BACKGROUND OF THE INVENTION

Weeds compete with crops for light, moisture, nutrients and space and consequently inhibit the production of foliage, fruit or seed of agricultural crops. The presence of weeds may also reduce the quality of the harvested crop and reduce harvesting efficiency. Weed control is essential for maximum production of many agronomic and horticultural crops including corn, (*Zea mays* L.), cotton (*Gossypium* SP), sunflower (*Helianthus annus* L.) and soybeans (*Glycine max* (L.) Merr.). Weeds on non-cropped areas may cause a fire hazard, undesirable drifting of sand or snow, or irritation to persons with allergies. Consequently, it is desirable to suppress growth of unwanted weeds.

While a large number of compounds exhibiting herbicidal activity are known, it is nonetheless advantageous to obtain additional compounds which effectively control the growth of unwanted vegetation.

Description of Related Art

U.S. Pat. No. 4,859,229 to Wenger discloses certain substituted 3-aryluracils having an ether (thio)carbamyloxy or sulphamyloxy substituent on the aromatic moiety, and weed control compositions based thereon. Compounds according to the present invention have different structures and effect greater selectivity to certain crops.

Lutz and Trotto in *J. Heterocyclic Chemistry*, (1972), 9, (3), 513 discuss means of synthesizing 6-(trifluoromethyl) cytosines and 6-(trifluoromethyl) uracils. It will become apparent that the compounds and processes disclosed in the above references differ significantly from those herein disclosed.

SUMMARY OF THE INVENTION

In one aspect, this invention relates to compounds of formula I below:

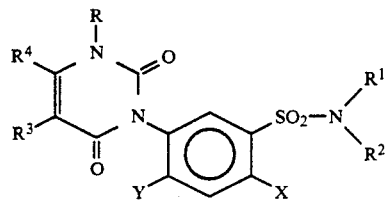

wherein:

R is hydrogen, $C_1$-$C_4$ alkyl, $C_1$-$C_4$ haloalkyl, formyl, $C_2$-$C_6$ alkanoyl, $C_3$-$C_4$ alkenyl or $C_3$-$C_4$ alkynyl, or alkali metal;

X is $C_1$-$C_4$ alkyl, $C_1$-$C_8$ alkoxy, cyano, or halogen;

Y is hydrogen, halogen, or $C_1$-$C_4$ dialkylamino;

$R^1$ is hydrogen, $C_1$-$C_8$ straight chain or branched alkyl, $C_3$-$C_8$ cycloalkyl, $C_3$-$C_8$ alkenyl, $C_3$-$C_8$ alkoxy or $C_3$-$C_8$ hydroxyalkyl;

$R^2$ is hydrogen, $C_1$-$C_8$ straight chain or branched alkyl, $C_3$-$C_8$ alkenyl, $C_3$-$C_8$ cycloalkyl, halo substituted $C_3$-$C_8$ alkenyl, $C_3$-$C_8$ alkynyl, $C_1$-$C_4$ alkoxy, hydroxy $C_1$-$C_4$ alkyl, cyano $C_1$-$C_4$ alkyl, 2,3-epoxypropyl, 2,2-dialkoxyethyl, alkoxyal phenyl, aralkyl, $C_1$-$C_4$ acyl, $C_1$-$C_4$ carbalkoxyalkyl, $C_1$-$C_4$ carbalkoxyalkyl substituted by $C_1$-$C_4$ alkyl, phenylmethyl or methylthioethyl, (1,3-dioxolan-2-yl)alkyl, dialkylaminoethyl, or tetrahydrofuranylmethyl;

$R^3$ is hydrogen, halogen or $C_1$-$C_4$ alkyl;

$R^4$ is $C_1$-$C_4$ alkyl or $C_1$-$C_4$ haloalkyl $R^1$ and $R^2$ taken together form a $C_3$-$C_8$ membered heterocyclic ring containing one or more heteroatoms; as well as salts of the compounds of formula I in which R is hydrogen or $R^1$ is hydrogen.

In another aspect, this invention relates to an herbicidal composition comprising:

(a) a compound having the structure of formula (I) above; and (b) a suitable carrier.

In yet another aspect of the present invention, a process (hereinafter referred to as "process A") for preparing the above-described class of compounds having the structural formula I is described. In the process of forming the above described class of compounds, with the proviso that R is an alkali metal, a compound having the structural formula

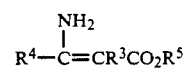

where $R^3$ is hydrogen or $C_1$-$C_4$ alkyl; $R^4$ is $C_1$-$C_4$ alkyl or $C_1$-$C_4$ haloalkyl; and $R^5$ is $C_1$-$C_6$ alkyl, is reacted with sodium hydride. The product of this reaction is further reacted with a novel isocyanatobenzenesulfonamide having the structural formula:

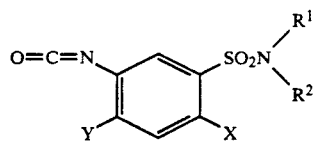

where X and Y have the meanings given above for the compound of this invention and with the proviso that $R^1$ and $R^2$ cannot be hydrogen. The product of formula I, where R is an alkali metal, may be isolated or further reacted to produce other compounds of formula I.

Additional compounds in accordance with this invention, where R is $C_1$-$C_4$ alkyl, $C_3$-$C_4$ alkenyl, $C_1$-$C_4$ haloalkyl, or $C_3$-$C_4$ alkynyl, are made by reacting a precursor compound of the present invention where R is an alkali metal, with an alkylating agent, R—Z, where R has the meanings defined above and Z represents a leaving group.

In further accordance with the process of making the compounds of this invention, a compound in which R is hydrogen is prepared by reacting a precursor compound of the present invention wherein R is an alkali metal, with a strong acid.

The novel isocyanatobenzenesulfonamide intermediate is prepared by phosgenation of the aminosubstituted benzenesulfonamide.

Another process (hereinafter referred to as "process B") for preparing the above described class of compounds having the structural formula I first involves the chlorosulfonation of certain 3-aryl substituted 2,4-(1H,3H)-pyrimidinediones having the structural formula

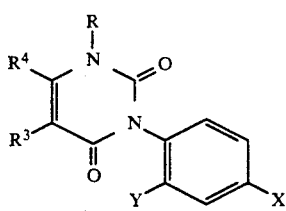

where R, $R^3$, $R^4$, X and Y have the meanings given above with the proviso that R is not alkali metal, formyl, alkanoyl, alkenyl or alkynyl, to produce novel pyrimidinyl substituted benzenesulfonyl chloride intermediates of the structural formula

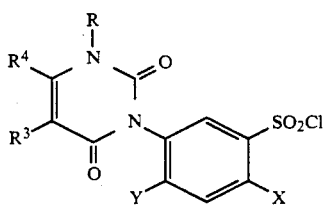

The pyrimidinyl substituted benzenesulfonyl chloride is then reacted with an appropriate amine to produce compounds of formula I.

In still further accordance with the instant invention another process (hereinafter referred to as "process C") for making the aforesaid compounds is carried out by reacting certain substituted pyrimidinylbenzenesulfonamides with an alkyl halide in the presence of sodium hydride in N, N-dimethylformamide or other suitable solvents.

In yet still further accordance with a process of making certain compounds of formula I (hereinafter referred to as process D), the products of process C may be hydrogenated over a palladium/carbon catalyst.

It has been found that certain of the aforedescribed [3,6-dihydro-2,6-dioxo-1(2H)-pyrimidinyl]benzenesulfonamides possess excellent herbicidal properties. These properties are surprisingly effective in both pre- and post-emergent applications. That is, the class of compounds of the present invention effectively controls undesired vegetation both prior to and after emergence from soil.

In still another aspect of the present invention, a method for controlling weeds and other undesirable vegetation is disclosed. In this method, an herbicidally effective amount of a compound having the structural formula I is applied to the locus to be protected along with a suitable carrier.

DETAILED DESCRIPTION OF THE INVENTION

The compositions of this invention contain compounds having the structural formula (I) shown below:

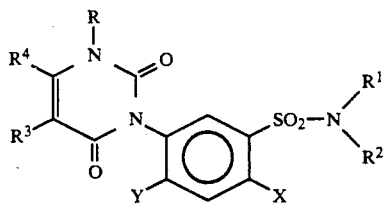

wherein:
R is hydrogen, $C_1$–$C_4$ alkyl, $C_1$–$C_4$ haloalkyl, formyl, $C_2$–$C_6$ alkanoyl, $C_3$–$C_4$ alkenyl or $C_3$–$C_{14}$ alkynyl, or alkali metal;
X is $C_1$–$C_4$ alkyl, $C_1$–$C_8$ alkoxy, cyano, or halogen;
Y is hydrogen, halogen, or $C_1$–$C_4$ dialkylamino;
$R^1$ is hydrogen, $C_1$–$C_8$ straight chain or branched alkyl, $C_3$–$C_8$ cycloalkyl, $C_3$–$C_8$ alkenyl, $C_3$–$C_8$ alkoxy or $C_3$–$C_8$ hydroxyalkyl;
$R^2$ is hydrogen, $C_1$–$C_8$ straight chain or branched alkyl, $C_3$–$C_8$ alkenyl, $C_3$–$C_8$ cycloalkyl, halo substituted $C_3$–$C_8$ alkenyl, $C_3$–$C_8$ alkynyl, $C_1$–$C_4$ alkoxy, hydroxy $C_1$–$C_4$ alkyl, cyano $C_1$–$C_4$ alkyl, 2,3-epoxypropyl, 2,2-dialkoxyethyl, alkoxyalkyl, phenyl, aralkyl, $C_1$–$C_4$ acyl, $C_1$–$C_4$ carbalkoxyalkyl, $C_1$–$C_4$ carbalkoxyalkyl substituted by $C_1$–$C_4$ alkyl, phenylmethyl or methylthioethyl, (1,3-dioxolan-2-yl)alkyl, dialkylaminoethyl, or tetrahydrofuranylmethyl;
$R^3$ is hydrogen, halogen or $C_1$–$C_4$ alkyl;
$R^4$ is $C_1$–$C_4$ alkyl or $C_1$–$C_4$ haloalkyl
$R^1$ and $R^2$ taken together form a $C_1$–$C_8$ membered heterocyclic ring containing one or more heteroatoms; as well as salts of the compounds of formula I in which R is hydrogen or $R^1$ is hydrogen.

Preferably, compounds according to the present invention have the structural formula I wherein R is $C_1$–$C_3$ alkyl or $C_3$–$C_4$ alkynyl; X is halogen or $C_1$–$C_3$ alkyl; Y is halogen or hydrogen; R is hydrogen or $C_1$–$C_3$ alkyl or $C_3$–$C_8$ hydroxyalkyl; $R^2$ is $C_1$–$C_3$ alkyl, $C_3$–$C_8$ cycloalkyl, $C_3$–$C_4$ alkenyl, alkoxylalkyl, aralkyl, hydroxy $C_1$–$C_4$ alkyl or 2,3-epoxypropyl, $R^3$ is hydrogen; and $R^4$ is trifluoromethyl.

Still more preferably, compounds according to the present invention have structural formula I wherein R is methyl; X is chlorine or fluorine; Y is fluorine or hydrogen; $R^1$ is hydrogen, methyl, or $C_1$–$C_4$ hydroxyalkyl; $R^2$ is hydrogen, $C_1$–$C_4$ alkyl, $C_3$–$C_6$ cycloalkyl, $C_1$–$C_4$ alkoxy, alkoxyalkyl, hydroxy $C_1$–$C_4$ alkyl, cyanoalkyl, 2,2-dialkoxyethyl, carbalkoxyalkyl, $R^3$ is hydrogen; and $R^4$ is trifluoromethyl.

Most preferably, compounds according to the instant invention have the structural formula I wherein R is methyl; X is chlorine; Y is hydrogen or fluorine; $R^1$ is methyl, ethyl, or hydrogen; $R^2$ is methyl, ethyl, methoxy, hydroxyethyl, acetyl, methoxyethyl, 2,2-dimethoxyethyl, 1-carbethoxyethyl, or 1-carbethoxy-2-methylpropyl; $R^3$ is hydrogen; and $R^4$ is trifluoromethyl.

The present invention is also directed to a composition having utility as an herbicidal agent which comprises a compound having the structural formula I and a suitable carrier therefor.

Preferably, compositions of the present invention comprise a compound having the structural formula I in which R,X,Y,R$^1$ and R$^2$ incorporate the embodiments indicated in the above described preferable compounds and a suitable carrier therefor.

Still more preferably, compositions of the present invention comprise a compound having the structural formula I where R,X,Y,R$^1$ and R$^2$ incorporate the embodiments disclosed for the above described still more preferable compounds and a suitable carrier therefor.

Most preferably, compositions of the present invention comprise a compound having the structural formula I where R,X,Y, R$^1$ and R$^2$ incorporate the embodiments disclosed for the above described most preferable compounds and a suitable carrier therefor.

The principal utility of the compositions of the present application are as herbicides and are made of:

(a) an herbicidally effective amount of a novel pyrimidylbenzenesulfonamide compound according to the present invention and (b) a suitable carrier.

Such compositions may comprise one or more of the novel pyrimidinylbenzenesulfonamides of this invention. To prepare such agriculturally useful compositions, the active ingredient(s) may be mixed with an adjuvant to provide compositions in the form of finely-divided particulate solids, granules, pellets, wettable powders, flowable liquids, soluble powders, solutions, and aqueous or organic solvent dispersions or emulsions. Such formulations may be of several different physical and chemical types which can be made by one with ordinary skill in the art. For instance, the agriculturally active compound may be impregnated on finely-divided or granular inorganic or organic carriers such as appapulgite clay, sand, vermiculite, corn cob, activated carbon or other granular carriers known to the art. The impregnated granules may then be spread on, or incorporated into the soil.

Alternatively, the active ingredient(s) may be formulated as a wettable powder by grinding into a fine powder and mixing with an inactive powdered carrier to which a surface active dispersing agent has been added. Typical powdered solid carriers are the various mineral silicates (such as mica, talc, pyrophyllite, clays and the like) or powdered organic materials (e.g., corn cob). The wettable powder may then be dispersed in water and sprayed on the soil surface, or on crop or weed plants.

Similarly, an emulsifiable concentrate may be prepared by dissolving the active ingredient(s) in a solvent such as naphtha, toluene, or other aromatic or aliphatic hydrocarbon to which a surface active dispersing agent generally has been added. The emulsifiable concentrate may then be dispersed in water and applied by spraying.

The concentration of active ingredient(s) in the composition may vary widely, typically ranging from about 1% to about 95% by weight. The concentration of active ingredient(s) in dispersions applied to the soil or foliage is typically between about 0.002% and about 80% by weight.

Formulations containing the active ingredient(s) may be dispersed in water or an organic liquid (such as oil) and applied to target plants. Surface active agents may be added to the solution to be applied to increase its qualitative or quantitative range of activity. Suitable surface active agents are well known to those skilled in the art. Reference may be made to McCutcheon's Detergents and Emulsifiers (1980, Allured Publ. Co., Ridgewood, N.J.) for examples of appropriate surface active agents. Similarly, such formulation may be applied to the soil either as a liquid or a granule.

In preemergence herbicidal applications, the compound of this invention is typically applied at a rate from about 0.01 to about 10 pounds per acre (about 0.01 to about 11 kg/ha) to soil which contains weed and crop seed. Such application is made either to the surface of the soil or into the upper one to three inches (2.5 to 7.5 cm.) of soil. When employed as a postemergence herbicide, the compound is typically applied at a rate of from about 0.01 to about 10 pounds per acre (about 0.01 to about 11 kg/ha) to the aerial portions of weeds.

The most suitable rate of application in any given case depends on such factors which include the plant species, the stage of plant development, the method of application, the specific biological effect desired, the air and soil temperature, soil type, soil pH, soil fertility, moisture, organic matter content, the condition and vigor of the target plants, the relative humidity and wind velocity of the air around the crop at the time of treatment, the extent and density of the foliar canopy of the target plant, the quantity and intensity of rainfall before and after treatment, light intensity and light duration per day. All of these factors can have an influence on the efficacy of the chemicals for a given weed control use. However, one skilled in the art can, by routine experimentation, readily determine optimum conditions for employment of any of the particular pyrimidinyl benzenesulfonamide compounds of this invention.

The herbicidal use may include control of vegetation at industrial sites or selective weed control in crop fields.

The following examples are intended to further illustrate the invention and are not intended to limit the scope of the invention in any manner.

The first set of examples (A-1 through A-6) are illustrative of process A for producing [3,6-dihydro-2,6-dioxo-1(2H)-pyrimidinyl]benzenesulfonamides by reacting an amino substituted benzenesulfonamide with excess phosgene in ethyl acetate to form an isocyanatobenzenesulfonamide intermediate, which is in turn reacted with an ester compound, e.g., ethyl-3-amino-4,4,4-trifluoro-2-butenoate in the presence of sodium hydride and then subsequently reacted with an acid to yield compounds of formula I where R is hydrogen. Suitable acids include mineral acids such as hydrochloric acid and sulfuric acid. Substituents R$^1$, R$^2$, R$^3$, R$^4$, R$^5$, X, Y and Z all have the meanings indicated above with the proviso that R$^1$ and R$^2$ are not hydrogen. Examples A-1 through A-3 depict known compounds which are used to make the novel products of Examples A-4 through A-6.

Products of the above reaction may, in turn, be reacted with alkylating compounds designated R-Z in basic conditions to yield further compounds of formula I. R has the meanings designated above and Z is a leaving group which may include, e.g., halogens, alkylsulfonates or arylsulfonates.

The general reaction scheme for process A is depicted below:

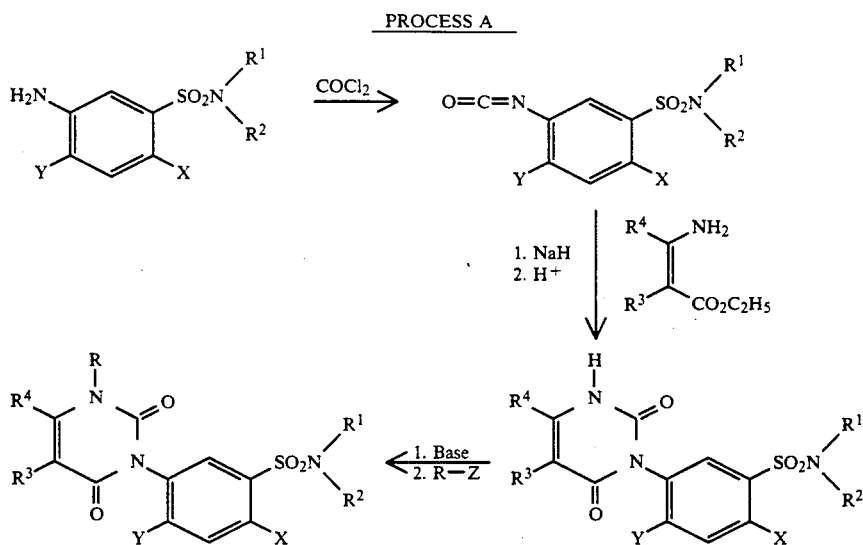

The second set of examples (B-1 through B-7) are illustrative of process B for producing [3,6-dihydro-2,6-dioxo-1(2H)-pyrimidinyl]benzenesulfonamides by chlorosulfonation of certain aryl substituted pyrimidinediones to form pyrimidinylbenzenesulfonyl chloride intermediates which are then reacted with an amine. Chlorosulfonation may be accomplished with chlorosulfonic acid. Substituent groups in this set of examples, namely, R, $R^1$, $R^2$, $R^3$, $R^4$, $R^5$, X, Y and Z, all have the meanings given above. If both X and Y are fluorine, the compounds of this reaction may be further reacted with an amine to form products wherein

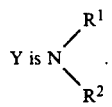

The reaction scheme for process B is generally depicted below:

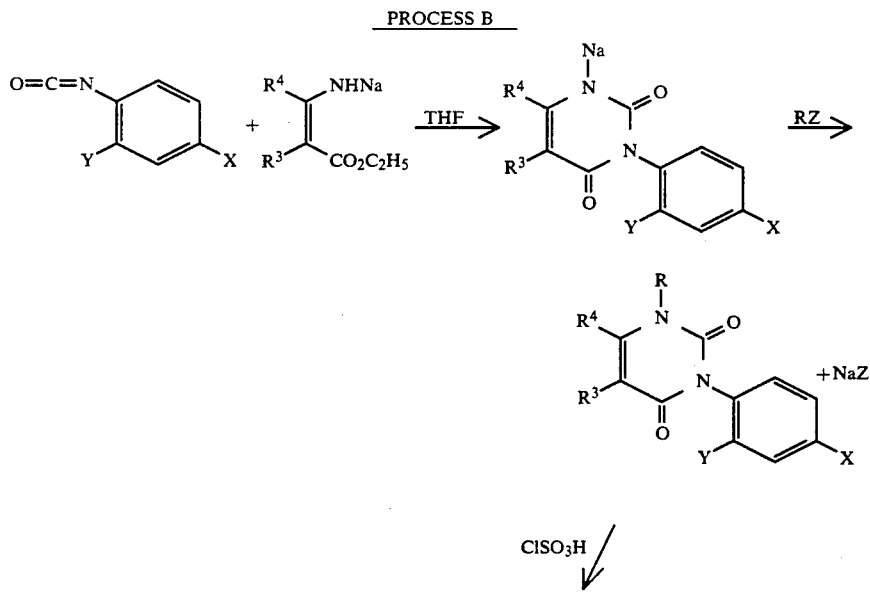

-continued
PROCESS B

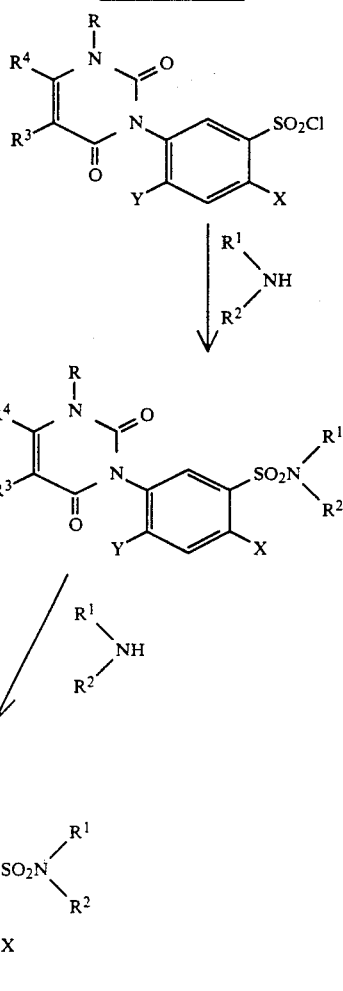

The third set of examples (C-1 and C-2) are illustrative of process C for producing [3,6-dihydro-2,6-dioxo-1(2H)-pyrimidinyl]benzenesulfonamides by reacting certain substituted pyrimidinylbenzenesulfonamides with an alkyl halide in the presence of sodium hydride in N,N-dimethylformamide. The reaction scheme for process C is generally depicted below:

PROCESS C

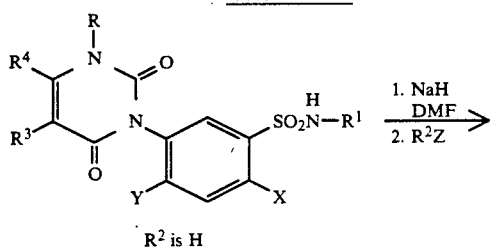

$R^2$ is H

-continued
PROCESS C

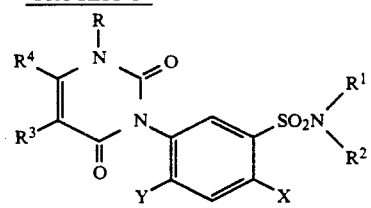

The fourth example (D-1) is illustrative of process D for producing [3,6-dihydro-2,6-dioxo-1(2H)-pyrimidinyl]benzenesulfonamides. In this process, the products of process C or certain other compounds of formula I may be hydrogenated over palladium/carbon catalyst. The reaction scheme for process D is generally depicted below:

PROCESS D

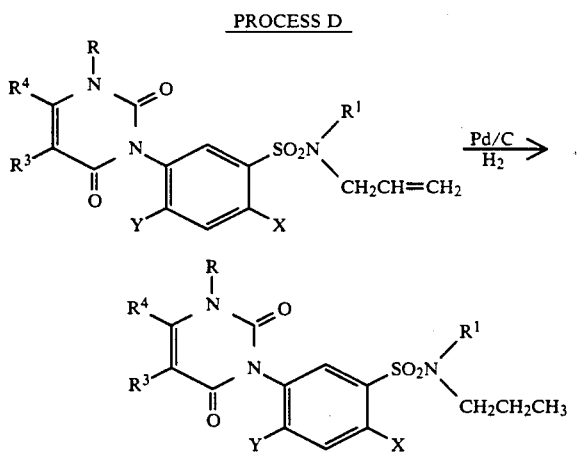

The fifth set of examples (Example V) illustrates the effectiveness of certain compounds of this invention as a preemergence herbicide.

The sixth set of examples (Example VI) illustrates the effectiveness of certain compounds of this invention as a postemergence herbicide.

I. Preparation of [3,6-dihydro-2,6-dioxo-(2H)pyrimidinyl]benzenesulfonamides by process A.

EXAMPLE A-1

Preparation of 2-chloro-5-nitrobenzenesulfonylchloride.

To a mixture of 104 g of commercially available sodium 2-chloro-5-nitrobenzenesulfonate, 200 ml of acetonitrile and 200 ml of sulfolane stirred at 25° C., was added 153 ml of phosphorus oxychloride over a period of 30 minutes. The temperature was not allowed to exceed 40° C. After completion of the addition, the reaction mixture was heated to 70° C. for 1.5 hours. On cooling to 0° C., the reaction mixture was poured over ice. The resulting solid product was washed with cold water, filtered and air-dried to give 77.6 g of the title compound with a melting point of 87°–89° C.

EXAMPLE A-2

Preparation of N,N-dimethyl-2-chloro-5-nitrobenzenesulfonamide.

To a solution of 80 g of 2-chloro-5-nitrobenzenesulfonyl chloride (Example A-1 above) in 200 ml of methylene chloride heated to reflux, was slowly added a solution of 30 g of dimethylamine hydrochloride in 30 ml of water followed by a dropwise addition of triethylamine. After completion of the addition, the reaction mixture was refluxed for 20 minutes, cooled to room temperature and concentrated by rotatory evaporation. The residue was treated with water and the resulting solid was filtered and recrystallized from ethanol, affording 61 g of the title compound, mp 138°–140° C.

EXAMPLE A-3

Preparation of N,N,-dimethyl-5-amino-2-chlorobenzenesulfonamide.

A mixture of 200 g of stannous chloride dihydrate and 250 ml of concentrated hydrochloric acid was cooled to 10° C. To the stirred mixture was added 50 g of N,N-dimethyl-2-chloro-5-nitrobenzenesulfonamide (Example A-2 above) in portions maintaining the temperature of 10° C. After removing the cooling bath, the reaction temperature rose to 55° C. and was held for two hours. The reaction mixture was cooled and filtered to remove the complex of the product with stannic chloride. The product was treated with water to decompose the complex and extracted with methylene chloride. Removal of solvent from the dried extract on a rotary evaporator gave 22 g of the title compound as a solid with a melting point of 125°–126° C.

EXAMPLE A-4

Preparation of N,N-dimethyl-2-chloro-5-isocyanatobenzenesulfonamide.

50 g of N,N-dimethyl-2-chloro-5-aminobenzene-sulfonamide (Example A-3 above) was treated with an excess of phosgene in ethyl acetate as is generally described in "Organic Functional Group Preparations" by S. R. Sandler and W. Karo on pages 364–365 (Academic Press, N.Y., 1983) (preparation of organic isocyanates), which disclosure is herein incorporated by reference. 48 g of the title compound was isolated as a tan solid with a melting point of 82°–85° C.

This compound is a novel intermediate in process A and is used in the preparation of several pyrimidinylbenzenesulfonamides of this invention. The structures of this and all previously synthesized intermediates were confirmed by NMR and IR spectroscopy.

EXAMPLE A-5

Preparation of N,N-dimethyl-2-chloro-5-[3,6-dihydro-4-trifluoromethyl-2,6-dioxo-1(2H)-pyrimidinyl]-benzenesulfonamide (Compound #5).

To 30 ml of dried tetrahydrofuran (THF) cooled to −5° C. was added, under nitrogen, 3.6 g of sodium hydride as a 60% dispersion mineral oil. To the stirred slurry was added a solution of 10 g of ethyl 3-amino-4,4,4-trifluoro-2-butenoate in 30 ml of THF over a period of 30 minutes. After stirring at −5° C. for 1 hour, the reaction mixture was cooled to −65° C. and a solution of N, N-dimethyl-2-chloro-5-isocyanatobenzenesulfonamide (Example A-4 above) in 30 ml of THF was added dropwise maintaining the temperature below −60° C. The mixture was stirred at −65° C. for 2 hours and allowed to warm to room temperature. After stirring for 17 hours, solvent was removed using a rotary evaporator. About 50 ml of water was added to the residue. The resulting mixture was filtered to remove a small amount of undissolved solid and the filtrate was acidified with hydrochloric acid. The resulting precipitate was filtered to give 13 g of the title compound as a beige solid, m.p. 281°–283° C.

Spectral data for this compound appears in Table I.

EXAMPLE A-6

Preparation of N,N-dimethyl-2-chloro-5-[3,6-dihydro-3-methyl-4-trifluoromethyl-2,6-dioxo-1(2H)-pyrimidinyl]benzenesulfonamide (Compound #6).

A mixture of 4.0 g of compound #5 (Example A-5 above), 1.7 g of sodium bicarbonate, 1.4 ml of dimethyl sulfate and 50 ml of acetone was heated to reflux for 3 hours. Filtration of the solids and evaporation of the solvent from the filtrate yielded a solid. The solid was washed with water and was recrystallized from ethanol to give 2.5 g of the title compound with a melting point of 194°–196° C.

II. Preparation of [3,6-dihydro-2,6-dioxo-1(2H)-pyrimidinyl]benzenesulfonamides by process B.

EXAMPLE B-1

Preparation of 3-(4-chloro-2-fluorophenyl)-6-trifluoromethyl-2,4(1H,3H)-pyrimidinedione, sodium salt compound with tetrahydrofuran (1:1).

Under a blanket of nitrogen, 21.2 g of a 60% dispersion of sodium hydride in mineral oil was washed three times with 50 ml of hexane. To a stirred slurry of sodium hydride and 300 ml of dried tetrahydrofuran (THF) cooled to −10° C., was added a solution of 100 g of ethyl 3-amino-4,4,4-trifluoro-2-butenoate in 400 ml of THF over a period of one hour. The temperature was held below −5° C. during the addition. The resulting clear brown solution was stirred an additional 15 minutes at −5° C. and then cooled to −70° C. using a Dry Ice/acetone bath. A solution of 91.5 g of 4-chloro-2-fluorophenyl isocyanate and 200 ml of THF was added over one hour while maintaining the temperature between −55° C. and −70° C. The reaction mixture was allowed to slowly warm to room temperature and was stirred at this temperature for 24 hours. A white solid separated and was filtered and washed with hexane to give 95.5 g of the title compound as a white powder with a melting point >300° C. An additional 57.2 g of the title compound was obtained by concentrating the filtrate to 200 ml and seeding with a small amount of crystals from the first crop. The NMR spectra of both crops were consistent with the structure of the title compound as a 1:1 molecular addition compound with THF.

The compound described in example B-1 is an intermediate of process B in the synthesis of [3,6-dihydro-2,6-dioxo-1(2H)-pyrimidinyl]benzenesulfonamides. Other examples may be found in Table B-1 following. NMR spectroscopy was used to confirm the structures of these compounds.

TABLE B-1

| Intermediate Compound # | X | Y | m | NMR (300 Mhz, DMSOd$_6$, δ) |
|---|---|---|---|---|
| A | CH$_3$ | H | 1 | 1.75 (m, 4H, CH$_2$), 2.32 (s, 3H, CH$_3$), 3.60 (m, 4H, CH$_2$), 5.58 (s, 1H, H$_5$), 6.39 (m, 2H, ArH), 7.15 (m, 2H, ArH) |
| B | Cl | H | 1 | 1.75 (m, 4H, CH$_2$), 3.60 (m, 4H, CH$_2$), 5.61 (s, 1H, H$_5$), 7.10 (m, 2H, ArH), 7.42 (m, 2H, ArH) |
| C | Br | H | 0.9 | 1.76 (m, 3.5H, CH$_2$), 3.60 (m, 3.5H, CH$_2$), 5.58 (s, 1H, H$_5$), 7.05 (m, 2H, ArH), 7.60 (m, 2H, ArH) |
| D | F | H | 1 | 1.75 (m, 4H, CH$_2$), 3.60 (m, 4H, CH$_2$), 5.61 (s, 1H, H$_5$), 7.15 (m, 4H, ArH) |
| E | F | F | 0.1[a] | 5.61 (s, 1H, H$_5$), 7.08 (m, 1H, ArH), 7.25 (m, 2H, ArH) |

[a] Sodium salt was soluble in THF. Methylene chloride was used to precipitate the product.

EXAMPLE B-2

Preparation of 3-(4-chloro-2-fluorophenyl)-1-methyl-6-trifluoromethyl-2,4-(1H,3H)-pyrimidinedione.

A mixture of 130 g of the product of Example B-1, 40 ml of iodomethane and 600 ml of acetone was stirred 18 hours at room temperature and then heated to a mild reflux for 8.5 hours. Volatiles were removed using a rotary evaporator. The solid residue was then partitioned between methylene chloride and water. The organic layer was washed with water and dried with magnesium sulfate. Rotary evaporation of the solvent gave an oil which was triturated with hexane. Filtration of the resulting solid gave 96.1 g of the title compound with a melting point of 114°–116° C.

The compound described in example B-2 is an intermediate of process B in the synthesis of [3,6-dihydro-2,6-dioxo-1(2H)-pyrimidinyl]benzenesulfonamides. Other examples may be found in Table B-2 following. NMR spectroscopy was used to confirm the structures of these compounds.

TABLE B-2

| Intermediate Compound # | X | Y | MP °C. | NMR (300 Mhz, CDCl$_3$, δ) |
|---|---|---|---|---|
| F | CH$_3$ | H | 122–124 | 2.39 (s, 3H, CH$_3$), 3.53 (d, 3H, CH$_3$), 6.35 (s, 1H, H$_5$), 7.08 (m, 2H, ArH), 7.29 (m, 2H, ArH) |
| G | Cl | H | 145–147 | 3.53 (d, 3H, CH$_3$), 6.35 (s, 1H, H$_5$), 7.14 (m, 2H, ArH), 7.46 (m, 2H, ArH) |
| H | F | F | 89–92 | 3.55 (d, 3H, CH$_3$), 6.36 (s, 1H, H$_5$), 7.00 (m, 2H, ArH), 7.25 (m, 1H, ArH) |
| I | F | H | 121–122.5 | 3.54 (d, 3H, CH$_3$), 6.36 (s, 1H, H$_5$), 7.18 (d, 4H, ArH) |
| J | Br | H | 158.5–161 | 3.54 (d, 3H, CH$_3$), 6.36 (s, 1H, H$_5$), 7.10 (m, 2H, ArH), 7.63 (m, 2H, ArH) |

EXAMPLE B-3

Preparation of 2-chloro-4-fluoro-5-[(3,6-dihydro-3-methyl-4-trifluoromethyl-2,6-dioxo-1(2H)-pyrimidinyl]benzenesulfonyl chloride.

To 85 ml of chlorosulfonic acid at room temperature was added, in portions, 50 g of the product of Example B-2, with stirring. The reaction solution was heated to 130° C. for four hours. Analysis of a hydrolyzed sample of the reaction mixture by thin layer chromatography (TLC) showed no starting material present. The mixture was cooled to 10° C. and very cautiously poured over a mixture of ice and methylene chloride. The organic layer was separated, washed with water and dried with magnesium sulfate. The solution containing the product was concentrated on a rotary evaporator and diluted with hexane forming a granular slurry. The product was filtered to give 52.5 g of the title compound as a light tan solid, melting point 121°–125° C.

The compounds listed in Table B-3 were prepared by the chlorosulfonation of the appropriately substituted 3-phenyl-2,4(1H,3H)-pyrimidinediones as described in the example above and are novel intermediates to prepare the desired [3,6-dihydro-2,6-dioxo-1(2H)-pyrimidinyl]benzenesulfonamides of this invention by process B. The structures of these compounds were confirmed by NMR spectroscopy.

TABLE B-3

| Intermediate Compound # | R | X | Y | MP °C. | NMR (300 Mhz, CDCl$_3$ δ) |
|---|---|---|---|---|---|
| K | CH$_3$ | CH$_3$ | H | 143–144 | 2.83 (s, 3H, CH$_3$), 3.55 (d, 3H, CH$_3$), 6.38 (s, 1H, H$_5$), 7.49 (dd, 1H, ArH$_4$), 7.54 (d, 1H, ArH$_3$) 7.95 (d, 1H, ArH$_6$) |
| L | H | CH$_3$ | H | 226–228 dec | (+DMSOd$_6$) 2.82 (s, 3H, CH$_3$), 6.17 (s, 1H, H$_5$), 7.57 (m, 2H, ArH$_{3,4}$), 7.98 (d, 1H, ArH$_6$), 12.6 (br, 1H, NH) |
| M | CH$_3$ | Cl | H | 180–185 | 3.55 (d, 3H, CH$_3$), 6.38 (s, 1H, H$_5$), 7.53 (dd, 1H, ArH$_4$), 7.76 (d, 1H, ArH$_3$), 8.03 (d, 1H, ArH$_6$) |
| N | CH$_3$ | Br | H | 176–179 | 3.52 (s, 3H, CH$_3$), 6.34 (s, 1H, H$_5$), 7.42 (dd, 1H, ArH$_4$), 7.95 (d, 1H, ArH$_3$), 8.04 (d, 1H, ArH$_6$) |
| O | CH$_3$ | F | H | 179–183 | 3.56 (s, 3H, CH$_3$), 6.39 (s, 1H, H$_5$), 7.46 (m, 1H, ArH), 7.60 (m, 1H, ArH), 7.88 (m, 1H, ArH$_6$) |
| P | CH$_3$ | F | F | 110–113 | 3.58 (d, 3H, CH$_3$), 6.39 (s, 1H, H$_5$) 7.26 (t, 1H, ArH$_3$), 7.97 (m, 1H, ArH$_6$) |

EXAMPLE B-4

Preparation of N,N-diethyl-2-chloro-4-fluoro-5-(3,6-dihydro-3-methyl-4-trifluoromethyl-2,6-dioxo-1(2H)pyrimidinyl)benzenesulfonamide (Compound #18).

To a solution of 1.5 ml of diethylamine and 20 ml of methylene chloride cooled to 5° C. as added, with stirring, a solution of 2.0 g of the product of Example B-3 and 10 ml of methylene chloride over 15 minutes. After 30 minutes the reaction mixture was poured into cold dilute sulfuric acid. The organic layer was separated and dried over magnesium sulfate. Removal of the volatiles by rotary evaporation gave 1.9 g of tan solid. Recrystallization of the product from ethanol afforded 1.8 g of the title compound, m.p. 190°–191° C. Spectral data for this compound is found in Table I.

EXAMPLE B-5

Preparation of N-ethyl-2-chloro-4-fluoro-5-(3,6-dihydro-3-methyl-4-trifluoromethyl-2,6,-dioxo-1(2H)pyrimidinyl)benzenesulfonamide (Compound #67).

To a solution of 2.0 g of the product of Example B-3 in 30 ml of methylene chloride cooled to 5° C. was added 0.8 ml of a 70% solution of ethylamine in water. After stirring 1 hour at 5° C., the reaction mixture was stirred 16 hours at room temperature. The product was isolated as a solid weighing 2.4 g following the procedure set forth in Example B-4 above. Recrystallization from ethanol gave 1.7 g of the title compound as a white crystalline solid with a melting point of 195°–196° C. Spectral data for this compound is found in Table I.

EXAMPLE B-6

Preparation of N-cyanomethyl-N-methyl-2-chloro-4-fluoro-5-(3,6-dihydro-3-methyl-4-trifluoromethyl-2,6-dioxo-1(2H)-pyrimidinyl)benzenesulfonamide (Compound #72).

To a stirred mixture of 2.0 g of the compound of Example B-3, 0.54 g of methylaminoacetonitrile hydrochloride and 30 ml of methylene chloride cooled to 5° C., was added a solution of 1.4 ml of triethylamine and 10 ml methylene chloride. The reaction mixture was stirred for 22 hours at room temperature and worked up as described in Example B-4. Evaporation of solvent produced 2.2 g of a foam which crystallized from isopropanol giving 1.8 g of the title compound as a beige solid, melting point 155°–157° C. Spectral data for this compound is found in Table I.

EXAMPLE B-7

Preparation of N, N-dimethyl-2-fluoro-4-dimethylamino-5-(3,6-dihydro-3-methyl-4-trifluoromethyl-2,6-dioxo-1(2H)-pyrimidinyl)benzenesulfonamide (Compound #50).

To a solution of 2.0 g of 2,4,-difluoro-5-(3,6-dihydro-3-methyl-4-trifluoromethyl-2,6-dioxo-1(2H) pyrimidinyl)benzenesulfonyl chloride and 30 ml of methylene chloride cooled to 5° C. was added 1.9 ml of a 40% solution of dimethylamine in water over 15 minutes. Analysis of the reaction mixture by TLC after 2 hours of stirring showed a single component. Work up was carried out as described in Example B-4. Two grams of crude solid was obtained and recrystallized from ethanol giving 1.7 g of a white solid, melting point 185°–194° C. NMR analysis of the product showed a 2:1 mixture of N,N-dimethyl-2,4-difluoro-5-(3,6-dihydro-3- methyl-4-trifluoromethyl-2,6-dioxo-1(2H)-pyrimidinyl)benzenesulfonamide (Compound #49) and the title compound. A mixture of 1.6 g of the product, 30 ml of methylene chloride and 3.8 ml of a 40% solution of dimethylamine in water was stirred at room temperature for 21 hours. The organic layer was separated, washed with water and dried over magnesium sulfate. After removal of volatiles using a rotary evaporator there remained 1.6 g of a solid. Recrystallization of the product from ethanol gave 1.4 g of the title compound as fine white crystals, m.p. 223.5°–225° C. Spectral data for this compound is found in Table I.

III. Preparation of [3,6-dihydro-2,6-dioxo-1(2H)-pyrimidinyl]benzenesulfonamides by Process C.

EXAMPLE C-1

Preparation of N-(2-methoxyethyl)-N-methyl-2-chloro-5-(3,6-dihydro-3-methyl-4-trifluoromethyl-2,6-dioxo-1(2H)-pyrimidinyl)benzenesulfonamide (Compound #53).

To a stirred slurry of 0.2 g of a 60% dispersion of sodium hydride in mineral oil and 30 ml of N,N-dimethylformamide (DMF) cooled to 5° C. was added 1.95 g of N-(2-methoxyethyl)-2-chloro-5-(3,6-dihydro-3-methyl-4-trifluoromethyl-2,6-dioxo-1(2H)-pyrimidinyl)benzenesulfonamide (Compound #52) prepared according to the procedure set forth above Process B using 2-chloro-5-(3,6-dihydro-3-methyl-4-trifluoromethyl-2,6-dioxo-1(2H)pyrimidinyl)benzenesulfonyl chloride and 2-methoxyethylamine. After stirring for 1 hour at 5° C., 0.6 ml of iodomethane was added to the reaction mixture. After stirring at room temperature for 16 hours, the mixture was concentrated using a rotary evaporator. The resulting gummy residue was treated several times with water until a solid had formed. The solid was recrystallized from ethanol to give 1.3 g of the title compound as a white crystalline solid, m.p. 108°–110° C. Spectral data for this compound is found in Table I.

EXAMPLE C-2

Preparation of N-acetyl-N-methyl-2-chloro-5-(3,6-dihydro-3-methyl-4-trifluoromethyl-2,6-dioxo-1(2H)pyrimidinyl)benzenesulfonamide (Compound #55).

To a stirred mixture of 0.16 g of a 60% dispersion of sodium hydride in mineral oil and 30 ml of DMF cooled to 5° C. was added 1.5 g of N-methyl-2-chloro-5-(3,6-dihydro-3-methyl-4-trifluoromethyl-2,6-dioxo-1(2H)-pyrimidinyl)benzenesulfonamide. (Compound #40), prepared from 2-chloro-5-(3,6-dihydro-3-methyl-4-trifluoromethyl-2,6-dioxo-1(2H)pyrimidinyl)benzenesulfonyl chloride and a 40% solution of methylamine in water following the procedure of Process B. After stirring for 1 hour at 5° C., 0.75 ml of acetic anhydride was added to the reaction mixture. After stirring at room temperature for 18 hours, the mixture was concentrated using a rotary evaporator. On treating the residue with cold water, 1.6 g of a brown solid was obtained. Further treatment of the solid with boiling ethanol and filtration gave 1.25 g of the title compound as an off-white solid, m.p. 193°–195° C. Spectral data for this compound is found in Table I.

IV. Preparation of [3,6-dihydro-2,6-dioxo-1(2H)pyrimidinyl]benzenesulfonamides by Process D.

EXAMPLE D-1

Preparation of N-methyl-N-propyl-2-chloro-5-(3,6-dihydro-3-methyl-4-trifluoromethyl-2,6-dioxo-1(2H)pyrimidinyl)benzenesulfonamide (Compound #38).

A mixture of 1.6 g of N-methyl-N-(2-propenyl)-2-chloro-5-(3,6-dihydro-3-methyl-4-trifluoromethyl-2,6-dioxo-1(2H)-pyrimidinyl)benzenesulfonamide (Compound #29), prepared by process C from Compound #28 and iodomethane, 100 ml of ethyl acetate and 200 mg of 5% palladium/carbon catalyst was hydrogenated in a Paar ® apparatus at 28 psi of hydrogen. After 30 minutes, the catalyst was filtered and solvent removed from the filtrate by rotary evaporation. The glassy residue was treated with ethanol to give 1.4 g of the title compound as a light gray powder, m.p. 143.5°–145° C.

Spectral data for this compound is found in Table I. Certain compounds described in Table I exhibited noncrystalline characteristics which are noted (when applicable) in the column designated M.P.° C. (melting point). Such characteristics are designated "foam", "glass" and "resins". "Foam" may result when solvent is forced out of the product under vacuum. "Glass" is a non-crystalline solid lacking a distinct melting point. "Resin" is a substantially clear, semi-solid amorphous substance.

TABLE I

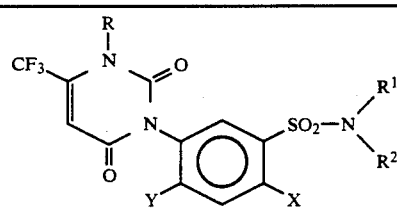

| COMPOUND No. | R | R¹ | R² | X | Y | MP °C. | NMR (SOLVENT) ppm | PROCESS METHOD OF PREPARATION |
|---|---|---|---|---|---|---|---|---|
| 1 | H | CH$_3$ | CH$_3$ | Cl | Cl | 288–290 | (Acetone$_6$) 2.87(s, 6H), 6.3(s, 1H), 7.61(m, 1H), 7.78(d, 1H), 8.05(s, 1H) | A |
| 2. | CH$_3$ | CH$_3$ | CH$_3$ | Cl | Cl | 221–223 | (CDCl$_3$) 2.9(s, 6H), 3.5 (s, 3H), 6.35(s, 1H), 7.7 (s, 1H), 8.01(s, 1H) | A |
| 3. | CH$_2$C≡CH | CH$_3$ | CH$_3$ | Cl | Cl | 223–225 | (CDCl$_3$) 2.3(d, 2H), 2.9(s, 6H) 4.7(s, 2H), 6.4(s, 1H), | A |

TABLE I-continued

| COMPOUND No. | R | R¹ | R² | X | Y | MP °C. | NMR (SOLVENT) ppm | PROCESS METHOD OF PREPARATION |
|---|---|---|---|---|---|---|---|---|
| 4. | CH₂CH=CH₂ | CH₃ | CH₃ | Cl | Cl | 171-173 | (CDCl₃) 2.9(s, 6H), 4.5 (q, 2H), 5.3(t, 2H), 6.0 (m, 1H), 6.3(s, 1H), 7.7 (s, 1H), 7.9(s, 1H) 7.8(s, 1H), 8.0(s, 1H) | A |
| 5. | H | CH₃ | CH₃ | Cl | H | 281-283 | (Acetoned₆) 2.85(s, 6H), 6.28(s, 1H), 7.65(d, 1H), 7.78(d, 1H), 8.05(s, 1H) | A |
| 6. | CH₃ | CH₃ | CH₃ | Cl | H | 194-196 | (CDCl₃) 2.9(s, 6H), 3.5 (s, 3H), 6.35(s, 1H), 7.41 (m, 1H), 7.6(m, 1H), 7.8 (m, 1H) | A |
| 7. | CH₂CH₃ | CH₃ | CH₃ | Cl | H | 148-149 | (CDCl₃) 1.36(t, 3H), 2.9 (s, 6H), 4.02(q, 2H), 6.35 (s, 1H), 7.38(m, 1H), 7.65 (d, 1H), 7.95(d, 1H) | A |
| 8. | Na | CH₃ | CH₃ | OCH₃ | H | >250 | (Dmsod₆) 2.75(s, 6H), 3.92(s, 3H), 5.62(s, 1H) 7.30(m, 3H) | A |
| 9. | H | CH₃ | CH₃ | OCH₃ | H | 247-249 | (Dmsod₆) 2.77(s, 6H), 3.96 (s, 3H), 6.33(s, 1H), 7.37 (d, 1H), 7.58(m, 1H), 7.73 (d, 1H), 12.5(brs, 1H) | A |
| 10. | CH₃ | CH₃ | CH₃ | OCH₃ | H | 168-170 | (Dmsod₆) 2.77(s, 6H), 3.39 (s, 3H), 3.96(s, 3H), 6.48 (s, 1H), 7.36(d, 1H), 7.55 (m, 1H), 7.70(d, 1H) | A |
| 11. | CH₃ | H | H | CH₃ | H | 231-232 | (Dmsod₆) 2.64(s, 3H), 3.39 (s, 3H), 6.49(s, 1H), 7.40 (dd, 1H), 7.48(m, 3H), 7.78 (d, 1H) | B |
| 12. | CH₃ | CH₃ | CH₃ | CH₃ | H | 148-150 | (CDCl₃) 2.67(s, 3H), 2.80 (s, 6H), 3.54(d, 3H), 6.35 (s, 1H), 7.33(m, 1H), 7.45 (d, 1H), 7.77(d, 1H) | B |
| 13. | CH₃ | C₂H₅ | C₂H₅ | CH₃ | H | 156-157 | (CDCl₃) 1.13(t, 6H), 2.65 (s, 3H), 3.32(q, 4H), 3.54 (d, 3H), 6.35(s, 1H), 7.30 (m, 1H), 7.41(d, 1H), 7.78 (d, 1H) | B |
| 14. | CH₃ | C₃H₇-i | H | CH₃ | H | 168-169 | (CDCl₃) 1.08(d, 6H), 2.68 (s, 3H), 3.50(m, 1H), 3.53 (d, 3H), 4.62(d, 1H), 6.35 (s, 1H), 7.31(m, 1H), 7.44 (d, 1H), 7.88(d, 1H) | B |
| 15. | CH₃ | C₄H₉-t | H | CH₃ | H | 178-180 | (CDCl₃) 1.22(s, 9H), 2.70 (s, 3H), 3.54(s, 3H), 4.77 (s, 1H), 6.35(s, 1H), 7.30 (m, 1H), 7.41(d, 1H), 7.90 (d, 1H) | B |
| 16. | CH₃ | CH₃ | CH₃ | Cl | F | 223-235 | (CDCl₃) 2.95(s, 6), 3.60 (s, 3H), 6.40(s, 1H), 7.46 (d, 1H), 8.06(d, 1H) | B |
| 17. | CH₃ | (CH₂)₄ | | CH₃ | H | 180-181 | (CDCl₃) 1.88(m, 4H), 2.69 (s, 3H), 3.31(m, 4H), 3.54 (d, 3H), 6.35(s, 1H), 7.30 (m, 1H), 7.44(d, 1H), 7.80 (d, 1H) | B |
| 18. | CH₃ | C₂H₅ | C₂H₅ | Cl | F | 190-191 | (CDCl₃) 1.15(t, 6H), 3.39 (q, 4H), 3.55(d, 3H), 6.35 (s, 1H), 7.42(d, 1H), 8.07 (d, 1H) | B |
| 19. | CH₃ | C₄H₉-n | C₄H₉-n | Cl | F | 135-136 | (CDCl₃) 0.88(t, 6H), 1.27 (m, 4H), 1.48(m, 4H) 3.29 | B |

TABLE I-continued

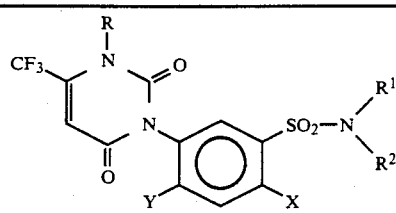

| COMPOUND No. | R | R¹ | R² | X | Y | MP °C. | NMR (SOLVENT) ppm | PROCESS METHOD OF PREPARATION |
|---|---|---|---|---|---|---|---|---|
| | | | | | | | (m, 4H), 3.55(d, 3H), 6.35 (s, 1H), 7.40(d, 1H), 8.05 (d, 1H) | |
| 20. | $CH_3$ | H | H | Cl | F | 257–258 | $(Dmsod_6)$ 3.41(s, 3H), 6.58 (s, 1H), 7.80(s, 2H), 7.94 (d, 1H), 8.20(d, 1H) | B |
| 21. | $CH_3$ | $CH_2CH=CH_2$ | $CH_2CH=CH_2$ | Cl | F | 162–164 | $(CDCl_3)$ 3.55(d, 3H), 3.92 (d, 4H), 5.20(m 4H), 5.68 (m, 2H), 6.35(s, 1H), 7.41 (d, 1H), 8.08(d, 1H) | B |
| 22. | $CH_3$ | $C_3H_7$-n | $C_3H_7$-n | Cl | F | 157–158 | $(CDCl_3)$ 0.84(t, 6H), 1.54 (m, 4H), 3.25(m, 4H), 3.55 (d, 3H), 6.35(s, 1H), 7.41 (d, 1H), 8.05(d, 1H) | B |
| 23. | $CH_3$ | $CH_3$ | $C_4H_9$-n | Cl | F | 142–143 | $(CDCl_3)$ 0.91(t, 3H), 1.32 (m, 2H), 1.54(m, 2H), 2.87 (s, 3H), 3.22(t, 2H), 3.55 (d, 3H), 6.35(s, 1H), 7.41 (d, 1H), 8.04(d, 1H) | B |
| 24. | $CH_3$ | \multicolumn{2}{c}{$(CH_2)_4$} | Cl | F | 254–255 | $(CDCl_3)$ 1.91(m, 4H), 3.41 (m, 4H), 3.56(d, 3H), 6.35 (s, 1H), 7.43(d, 1H), 8.05 (d, 1H) | B |
| 25. | $CH_3$ | $CH_3$ | $CH_2CH_2OH$ | Cl | F | 163–164 | $(CDCl_3)$ 2.98(s, 3H), 3.38 (t, 2H), 3.55(d, 3H), 3.70 (m, 2H), 4.17(t, 1H), 6.36 (s, 1H), 7.48(d, 1H), 8.07 (d, 1H) | B |
| 26. | $CH_3$ | $CH_3$ | $CH_2C_6H_5$ | Cl | F | 135–136 | $(CDCl_3)$ 2.75(s, 3H), 3.55 (d, 3H), 4.42(m, 2H), 6.35 (s, 1H), 7.31(m, 5H), 7.44 (d, 1H), 8.09(d, 1H) | B |
| 27. | $CH_3$ | $CH_3$ | $C_6H_{11}$-c | Cl | F | 189–190 | $(CDCl_3)$ 0.95–1.82(m, 10H) 2.83(s, 3H), 3.55(d, 3H), 3.68(m, 1H), 6.35(s, 1H), 7.41(d, 1H), 8.06(d, 1H) | B |
| 28. | $CH_3$ | H | $CH_2CH=CH_2$ | Cl | H | 168–170 | $(CDCl_3)$ 3.53(d, 3H), 3.60 (m, 2H), 5.12(m, 2H), 5.71 (m, 1H), 6.35(s, 1H), 7.40 (m, 2H), 7.64(d, 1H), 7.94 (d, 1H) | B |
| 29. | $CH_3$ | $CH_3$ | $CH_2CH=CH_2$ | Cl | H | 145–146 | $(CDCl_3)$ 2.83(s, 3H), 3.54 (d, 3H), 3.86(d, 2H), 5.25 (m, 2H), 5.77(m, 1H), 6.35 (s, 1H), 7.35(dd, 1H), 7.63 (d, 1H), 7.97(d, 1H) | C |
| 30. | $CH_3$ | H | $C_3H_7$-i | Cl | H | 193–194 | $(CDCl_3)$ 1.10(d, 6H), 3.49 (m, 1H), 3.54(d, 3H), 4.94 (d, 1H), 6.36(s, 1H), 7.37 (dd, 1H), 7.64(d, 1H), 7.99 (d, 1H) | B |
| 31. | $CH_3$ | $CH_3$ | $C_3H_7$-i | Cl | H | 172–175 | $(CDCl_3)$ 1.12(d, 6H), 2.82 (s, 3H), 3.54(d, 3H), 4.15 (m, 1H), 6.35(s, 1H), 7.33 (dd, 1H), 7.61(d, 1H), 7.98 (d, 1H) | C |
| 32. | $CH_3$ | $C_2H_5$ | $C_2H_5$ | Cl | H | 181–182 | $(CDCl_3)$ 1.14(t, 6H), 3.39 (q, 4H), 3.54(d, 3H), 6.35 (s, 1H), 7.33(dd, 1H), 7.61 (d, 1H), 7.97(d, 1H) | B |
| 33. | $CH_3$ | $CH_3$ | $CH_2C\equiv CH$ | Cl | H | 131–133 | $(CDCl_3)$ 2.25(t, 1H), 2.96 (s, 3H), 3.54(d, 3H), 4.13 (d, 2H), 6.35(s, 1H), 7.36 (dd, 1H), 7.63(d, 1H), 7.97 (d, 1H) | B |
| 34. | $CH_3$ | H | $C_3H_5$-c | Cl | H | 190–191 | $(CDCl_3)$ 0.63(m, 4H), 2.24 | B |

TABLE I-continued

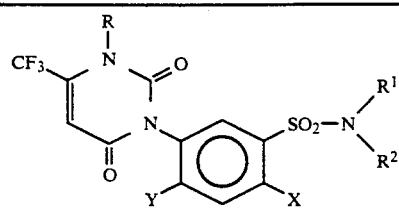

| COMPOUND No. | R | R¹ | R² | X | Y | MP °C. | NMR (SOLVENT) ppm | PROCESS METHOD OF PREPARATION |
|---|---|---|---|---|---|---|---|---|
| | | | | | | | (m, 1H), 3.54(d, 3H), 5.43 (s, 1H), 6.36(s, 1H), 7.41 (dd, 1H), 7.65(d, 1H), 8.03 (d, 1H) | |
| 35. | $CH_3$ | $CH_3$ | $C_3H_5$-c | Cl | H | 139–141 | ($CDCl_3$) 0.67(m, 4H), 2.27 (m, 1H), 2.99(s, 3H), 3.54 (d, 3H), 6.34(s, 1H), 7.38 (dd, 1H), 7.64(d, 1H), 8.00 (d, 1H) | C |
| 36. | $CH_3$ | $CH_3$ | $C_6H_5$ | Cl | H | 170–171 | ($CDCl_3$) 3.38(s, 3H), 3.51 (d, 3H), 6.31(s, 1H), 7.18–7.37(m, 6H), 7.61(d, 1H), 7.77(d, 1H) | B |
| 37. | $CH_3$ | H | $C_6H_5$ | Cl | H | 225–226 | ($CDCl_3$) 3.51(s, 3H), 6.33 (s, 1H), 7.10(m, 5H), 7.38 (dd, 1H), 7.56(d, 1H), 8.03 (d, 1H), 10.21(s, 1H) | B |
| 38. | $CH_3$ | $CH_3$ | $C_3H_7$-n | Cl | H | 143–145 | ($CDCl_3$) 0.89(t, 3H), 1.59 (m, 2H), 2.88(s, 3H), 3.22 (t, 2H), 3.54(d, 3H), 6.35 (s, 1H), 7.35(dd, 1H), 7.62 (d, 1H), 7.95(d, 1H) | D |
| 39. | $CH_3$ | $CH_3$ | $CH_2CH(OCH_3)_2$ | Cl | H | glass | ($CDCl_3$) 2.99(s, 3H), 3.38 (s+d, 8H), 3.54(d, 3H), 4.47(t, 1H), 6.36(s, 1H), 7.36(dd, 1H), 7.64(d, 1H), 7.96(d, 1H) | B |
| 40. | $CH_3$ | H | $CH_3$ | Cl | H | 210–212 | ($CDCl_3$) 2.64(d, 3H), 3.54 (d, 3H), 6.36(s, 1H), 6.44 (q, 1H), 7.39(dd, 1H), 7.65 (d, 1H), 7.95(d, 1H) | B |
| 41. | $CH_3$ | $CH_3$ | $CH_2CO_2C_2H_5$ | Cl | H | 130–132 | ($CDCl_3$) 1.24(t, 3H), 2.99 (s, 3H), 3.51(s, 3H), 4.16 (s+q, 4H), 6.35(s, 1H), 7.37(dd, 1H), 7.63(d, 1H), 7.98(d, 1H) | C |
| 42. | $CH_3$ | $CH_3$ | $CH_2C(Cl)=CH_2$ | Cl | H | 138–140 | ($CDCl_3$) 2.88(s, 3H), 3.55 (d, 3H), 4.10(s, 2H), 5.40 (m, 1H), 5.47(m, 1H), 6.36 (s, 1H), 7.38(dd, 1H), 7.65 (d, 1H), 7.98(d, 1H) | C |
| 43. | $CH_3$ | $CH_3$ | $C_2H_5$ | Cl | H | 156–158 | ($CDCl_3$) 1.18(t, 3H), 2.91 (s, 3H), 3.32(q, 2H), 3.55 (d, 3H), 6.36(s, 1H), 7.35 (dd, 1H), 7.63(d, 1H), 7.96 (d, 1H) | B |
| 44. | $CH_3$ | $CH_3$ | $CH_2CN$ | Cl | H | 170–171 | ($CDCl_3$) 2.98(s, 3H), 3.55 (d, 3H), 4.32(s, 2H), 6.36 (s, 1H), 7.43(dd, 1H), 7.68 (d, 1H), 7.98(d, 1H) | B |
| 45. | $CH_3$ | $CH_3$ | $OCH_3$ | Cl | H | 223–234 | ($CDCl_3$) 2.96(s, 3H), 3.55 (d, 3H), 3.74(s, 3H), 6.36 (s, 1H), 7.44(dd, 1H), 7.69 (d, 1H), 7.92(d, 1H) | B |
| 46. | $CH_3$ | $CH_3$ | $CH_2CH_2OH$ | Cl | H | 134–137 | ($CDCl_3$) 2.21(bs, 1H), 3.00 (s, 3H), 3.40(t, 2H), 3.54 (d, 3H), 3.73(t, 2H), 6.36 (s, 1H), 7.36(dd, 1H), 7.64 (d, 1H), 7.97(d, 1H) | B |
| 47. | $CH_3$ | $CH_3$ | $CH_3$ | F | H | 170–172 | ($CDCl_3$) 2.85(d, 6H), 3.55 (d, 3H), 6.36(s, 1H), 7.34 (t, 1H), 7.43(m, 1H), 7.75 (dd, 1H) | B |
| 48. | $CH_3$ | $CH_3$ | $CH_3$ | Br | H | 205–207 | ($CDCl_3$) 2.91(s, 6H), 3.55 (d, 3H), 6.36(s, 1H), 7.27 (dd, 1H), 7.86(d, 1H), 7.96 | B |

TABLE I-continued

Structure: 1-R, 3-(aryl with SO2-NR1R2, X, Y substituents), 6-CF3 uracil

| COMPOUND No. | R | R¹ | R² | X | Y | MP °C. | NMR (SOLVENT) ppm | PROCESS METHOD OF PREPARATION |
|---|---|---|---|---|---|---|---|---|
| 49. | $CH_3$ | $CH_3$ | $CH_3$ | F | F | 205-207 | ($CDCl_3$) 2.85(d, 6H), 3.56 (d, 3H), 6.36(s, 1H), 7.14 (t, 1H), 7.85(t, 1H) (d, 1H) | B |
| 50. | $CH_3$ | $CH_3$ | $CH_3$ | F | $N(CH_3)_2$ | 223-225 | ($CDCl_3$) 2.78(s, 6H), 2.82 (s, 6H), 3.54(d, 3H), 6.34 (s, 1H), 7.10(d, 1H), 7.60 (d, 1H), | B |
| 51. | $CH_3$ | $CH_3$ | $C_4H_9$-n | Cl | H | 140-142 | ($CDCl_3$) 0.90(t, 3H), 1.32 (m, 2H), 1.55(m, 2H), 2.88 (s, 3H), 3.25(t, 2H), 3.55 (d, 3H), 6.36(s, 1H), 7.34 (dd, 1H), 7.63(d, 1H), 7.95 (d, 1H) | B |
| 52. | $CH_3$ | H | $CH_2CH_2OCH_3$ | Cl | H | 119-121 | ($CDCl_3$) 3.18(m, 2H), 3.24 (s, 3H), 3.36(t, 2H), 3.55 (s, 3H), 5.47(t, 1H), 6.36 (s, 1H), 7.38(dd, 1H), 7.65 (d, 1H), 7.97(d, 1H) | B |
| 53. | $CH_3$ | $CH_3$ | $CH_2CH_2OCH_3$ | Cl | H | 108-110 | ($CDCl_3$) 2.99(s, 3H), 3.30 (s, 3H), 3.47(t, 2H), 3.55 (s+m, 5H), 6.38(s, 1H), 7.34(dd, 1H), 7.64(d, 1H), 7.95(d, 1H) | C |
| 54. | $CH_3$ | $CH_3$ | $CH_2CH\underset{\diagup O \diagdown}{\text{---}}CH_2$ (epoxide) | Cl | H | foam | ($CDCl_3$) 2.56(m, 1H), 2.78 (m, 1H), 2.99(s, 3H), 3.10 (m, 2H), 3.55(d, 3H), 3.80 (m, 1H), 6.36(s, 1H), 7.38 (dd, 1H), 7.65(d, 1H), 7.97 (d, 1H) | C |
| 55. | $CH_3$ | $CH_3$ | $C(O)CH_3$ | Cl | H | 193-195 | ($CDCl_3$) 2.35(s, 3H), 3.32 (s, 3H), 3.55(s, 3H), 6.36 (s, 1H), 7.45(dd, 1H), 7.66 (d, 1H), 8.09(d, 1H) | c |
| 56. | $CH_3$ | H | $\underset{\mid}{CH_3}$<br>$CHCO_2C_2H_5$ | Cl | F | glass | ($CDCl_3$) 1.20(td, 3H), 1.41 (dd, 3H), 3.55(s, 3H), 4.08(m, 3H), 5.81(m, 1H), 6.35+6.36(2s, 1H), 7.44(d, 1H), 8.01 (d, 1H) | B |
| 57. | $CH_3$ | H | $\underset{\mid}{CH_2C_6H_5}$<br>$CHCO_2C_2H_3$ | Br | H | foam | ($CDCl_3$) 3.08(m, 2H), 3.54 (s, 6H), 4.29(m, 1H), 5.72 (d, 1H), 6.35(s, 1H), 7.08-7.25(m, 6H), 7.76(d, 1H), 7.91(d, 1H) | B |
| 58. | $CH_3$ | H | $\underset{\mid}{C_3H_7\text{-}i}$<br>$CHCO_2C_2H_5$ | Cl | F | foam | ($CDCl_3$) 0.92(m, 6H), 1.16 (m, 3H), 2.10(m, 1H), 3.55 (s, 3H), 3.83(m, 1H), 4.02 (m, 2H), 5.67(d, 1H), 6.35 (d, 1H), 7.43(d, 1H), 7.97 (d, 1H) | B |
| 59. | $CH_3$ | H | $\underset{\mid}{CH_2CH_2SCH_3}$<br>$CHCO_2C_2H_5$ | Br | H | foam | ($CDCl_3$) 1.18(td, 3H), 2.07(s+m, 5H), 2.58(t, 2H), 3.56 (s, 3H), 4.10(q+m, 3H), 6.08(d, 1H), 6.37(s, 1H), 7.32(dd, 1H), 7.88(dd, 1H), 7.98(dd, 1H) | |
| 60. | $CH_3$ | H | $CH_2CH_2CO_2C_2H_5$ | Cl | H | glass | ($CDCl_3$) 1.27(t, 3H), 2.53 (t, 2H), 3.25(q, 2H), 3.56 | B |

TABLE I-continued

| COMPOUND No. | R | R¹ | R² | X | Y | MP °C. | NMR (SOLVENT) ppm | PROCESS METHOD OF PREPARATION |
|---|---|---|---|---|---|---|---|---|
| | | | | | | | (s, 3H), 4.16(q, 2H), 5.89 (t, 1H), 6.37(s, 1H), 7.43 (m, 1H), 7.66(d, 1H), 7.99 (d, 1H) | |
| 61. | H | CH₃ | CH₃ | CH₃ | H | 310 dec | (Dmsod₆) 2.60(s, 3H), 2.73 (s, 6H), 6.33(s, 1H), 7.52 (m, 2H), 7.75(s, 1H), 12.5 (brs, 1H) | B |
| 62. | H | H | C₂H₅ | CH₃ | H | 240–242 | (Dmsod₆) 0.99(t, 3H), 2.62 (S, 3H), 2.85(m, 2H), 6.32 (s, 1H), 7.47(m, 2H), 7.70 (t, 1H), 7.78(s, 1H), 12.5 (s, 1H) | B |
| 63. | H | CH₃ | C₂H₅ | CH₃ | H | 247–250 | (Dmsod₆) 1.09(t, 3H), 2.58 (s, 3H), 2.77(s, 3H), 3.19 (q, 2H), 6.33(s, 1H), 7.50 (m, 2H), 7.75(s, 1H), 12.5 (s, 1H) | B |
| 64. | H | H | C₃H₇-i | CH₃ | H | 217–220 | (Dmsod₆) 0.98(d, 6H), 2.62 (s, 3H), 3.27(m, 1H), 6.32 (s, 1H), 7.46(m, 2H), 7.68 (d, 1H), 7.81(s, 1H), 12.5 (s, 1H) | B |
| 65. | H | H | CH₂CH₂OCH₃ | CH₃ | H | 238–240 | (Dmsod₆) 2.61(s, 3H), 2.97 (q, 2H), 3.11(s, 3H), 3.28 (t, 2H), 6.32(s, 1H), 7.47 (m, 2H), 7.78(d, 1H), 7.85 (t, 1H), 12.5(s, 1H) | B |
| 66. | CH₃ | CH₃ | C₂H₅ | Cl | F | 190–191 | (CDCl₃) 1.18(t, 3H), 2.90 (s, 3H), 3.31(q, 2H), 3.56 (d, 3H), 6.36(s, 1H), 7.42 (d, 1H), 8.04(d, 1H) | B |
| 67. | CH₃ | H | C₂H₅ | Cl | F | 195–196 | (CDCl₃) 1.11(t, 3H), 3.00 (m, 2H), 3.55(s, 3H), 6.37 (s, 1H), 7.17(t, 1H), 7.46 (d, 1H), 8.06(d, 1H) | B |
| 68. | CH₃ | H | CH₃ | Cl | F | 187–189 | (CDCl₃) 2.62(d, 3H), 3.55 (s, 3H), 6.37(s, 1H), 7.08 (d, 1H), 7.47(d, 1H), 8.05 (d. 1H) | B |
| 69. | CH₃ | CH₃ | CH₂C≡CH | Cl | F | 178–179 | (CDCl₃) 2.26(t, 1H), 2.97 (s, 3H), 3.56(d, 3H), 4.12 (d, 2H), 6.36(s, 1H), 7.43 (d, 1H), 8.05(d, 1H) | B |
| 70. | CH₃ | H | C₃H₅-c | Cl | F | 187–190 | (CDCl₃) 0.50(m, 4H), 2.27 (m, 1H), 3.52(s, 3H), 6.41(s, 1H), 7.62(d, 1H), 8.18(d+s, 2H) | B |
| 71. | CH₃ | CH₃ | CH₂CH(OCH₃)₂ | Cl | F | glass | (CDCl₃) 2.99(s, 3H), 3.38 (s+m, 8H), 3.56(d, 3H), 4.47(t, 1H), 6.36(s, 1H), 7.44(d, 1H), 8.02(d, 1H) | B |
| 72. | CH₃ | CH₃ | CH₂CN | Cl | F | 155–157 | (CDCl₃) 2.98(s, 3H), 3.56 (d, 3H), 4.32(s, 2H), 6.37 (s, 1H), 7.48(d, 1H), 8.07 (d, 1H) | B |
| 73. | CH₃ | CH₃ | OCH₃ | Cl | F | 167–169 | (CDCl₃) 2.94(s, 3H), 3.56 (d, 3H), 3.74(s, 3H), 6.36 (s, 1H), 7.48(d, 1H), 8.00 (d, 1H) | B |
| 74. | CH₃ | H | CH₂CH₂OCH₃ | Cl | F | 170–172 | (CDCl₃) 3.17(m, 2H), 3.25 (s, 3H), 7.37(t, 2H), 3.56 (s, 3H), 5.48(t, 1H), 6.36 (s, 1H), 7.45(d, 1H), 8.05 (d, 1H) | B |
| 75. | CH₃ | CH₃ | CH₂CH₂OCH₃ | Cl | F | oil | (CDCl₃) 3.00(s, 3H), 3.31 | C |

TABLE I-continued

Structure: pyrimidine-2,4-dione with CF₃ and R on N, attached to phenyl ring bearing Y, X, and SO₂-NR¹R²

| COMPOUND No. | R | R¹ | R² | X | Y | MP °C. | NMR (SOLVENT) ppm | PROCESS METHOD OF PREPARATION |
|---|---|---|---|---|---|---|---|---|
| | | | | | | | (s, 3H), 3.48(m, 2H), 3.55 (m, 5H), 6.37(s, 1H), 7.45 (d, 1H), 8.06(d, 1H) | |
| 76. | $CH_3$ | CH₂CH₂OCH₂CH₂ (cyclic) | | Cl | F | 203–204 | (CDCl₃) 3.29(t, 4H), 3.56(s, 3H), 3.73(t, 4H), 6.36(s, 1H), 7.45(d, 1H), 8.02(d, 1H) | B |
| 77. | $CH_3$ | $CH_2CH_2OH$ | $CH_2CH_2OH$ | Cl | F | 160–164 | (CDCl₃) 3.48, 3.55, 3.62(t+s+brs, 9H), 3.78(t, 4H), 6.36(s, 1H), 7.44(d, 1H), 8.06(d, 1H) | B |
| 78. | $CH_3$ | $CH_3$ | $CH_2CH_2CN$ | Cl | F | foam | (CDCl₃) 2.69(t, 2H), 3.00(s, 3H), 3.56(d, 3H), 3.60(t, 2H), 6.36(s, 1H), 7.46(d, 1H), 8.05(d, 1H) | |
| 79. | $CH_3$ | $CH_3$ | CH₂CH(OCH₂)₂O (dioxolane) | Cl | F | foam | (CDCl₃) 3.00(s, 3H), 3.47(t, 2H), 3.56(d, 3H), 3.88(m, 4H), 5.04 (t, 1H), 6.36(s, 1H), 7.42(d, 1H), 8.05(d, 1H) | |
| 80. | $CH_3$ | H | $CH_2CH(OCH_3)_2$ | Cl | F | foam | (CDCl₃) 3.13(t, 2H), 3.30(d, 6H), 3.56(d, 3H), 4.25(t, 1H), 5.33(t, 1H), 6.36(s, 1H), 7.45(d, 1H), 8.03(d, 1H) | |
| 81. | $CH_3$ | $CH_3$ | $CH_2CH(OCH_3)_2$ | Br | H | foam | (CDCl₃) 2.98(s, 3H), 3.39(s+m, 8H), 3.55(d, 3H), 4.47(t, 1H), 6.36(s, 1H), 7.28(dd, 1H), 7.86(d, 1H), 7.97(d, 1H) | |
| 82. | $CH_3$ | $CH_3$ | $CH_2CH(OCH_3)_2$ | F | H | resin | (CDCl₃) 2.99(d, 3H), 3.30 (d, 2H), 3.39(s, 6H), 3.56 (d, 3H), 4.49(t, 1H), 6.37 (s, 1H), 7.30–7.48 (m, 2H), 7.79 (dd, 1H) | |
| 83. | $CH_3$ | $CH_3$ | CH₂CH(OCH₂)₂O (dioxolane) | Br | H | foam | (CDCl₃) 2.99(s, 3H), 3.50(d, 2H), 3.54(d, 3H), 3.90(m, 4H), 5.06(t, 1H), 6.35(s, 1H), 7.26(dd, 1H), 7.99(d, 1H) | |
| 84. | $CH_3$ | $CH_3$ | $CH_2CHO$ | Cl | F | foam | (CDCl₃) 2.96(s, 3H), 3.56 (d, 3H), 4.17(s, 2H), 6.37(s, 1H), 7.46(d, 1H), 8.06(d, 1H), 9.64(s, 1H) | |
| 85. | $CH_3$ | $CH_3$ | $CH_2CH(OCH_3)_2$ | F | F | resin | (CDCl₃) 2.99(d, 3H), 3.29(dd, 2H), 3.39(d, 6H), 3.57(d, 3H), 4.49(t, 1H), 6.37(s, 1H), 7.15(t, 1H), 7.87(t, 1H) | |

V. Preemergence Control

To illustrate the effectiveness of the compounds of this invention as preemergence herbicides, 300 mg of each of the below listed compounds were dissolved in 10 ml acetone to which 30 mg of an emulsifying agent, ethoxylated sorbitan monolaurate, were added. The solution was diluted to 100 ml with distilled water. Ten milliliters of the 3000 ppm solution were diluted to 250 ppm with distilled water. The chemical was applied at the rate of 10 lb/A (11.2 kg/ha) by drenching 46 ml of the 250 ppm solution on the surface of soil in 4 ½ inch (11.25 cm) plastic pots wherein seeds of the following weeds had been planted: Prickly sida (*Sida spinosa* L.) (PS), jimsonweed (*Datura stramonium* L. (JW), tall morningglory (*Ipomea purpurea* L. Roth) (TM), switchgrass (*Panicum virgatum* L.) (SG), barnyardgrass (*Echinochloa crusgalli* L. Beauv.) (BG), and green foxtail (*Setaria viridis* (L.), Beauv.) (GF). The percent control of the weeds compared to untreated checks was determined two weeks after treatment. The results of such testing are summarized in Table II. The data presented in such table indicated the good to excellent herbicidal efficacy of the compounds of this invention.

TABLE II

Preemergence Activity of 10 lb/A (11.2 kg/ha)
Percent Weed Control at 11.2 kg/ha

| Compound # | VL | JW | PS | TM | SG | BG | GF |
|---|---|---|---|---|---|---|---|
| 1 | 0 | 0 | — | 0 | 35 | 50 | 20 |
| 2 | 100 | 100 | — | 100 | 95 | 90 | 100 |
| 3 | 0 | 0 | — | 0 | 0 | 0 | 0 |
| 4 | 0 | 0 | — | 0 | 0 | 0 | 0 |
| 5 | 0 | 0 | — | 50 | 75 | 0 | 65 |
| 6 | 100 | 100 | — | 100 | 100 | 100 | 100 |
| 7 | 100 | 100 | — | 100 | 100 | 95 | 100 |
| 8 | 0 | 0 | — | 0 | 0 | 0 | 0 |
| 9 | 0 | 0 | — | 0 | 0 | 0 | 0 |
| 10 | 100 | 0 | — | 100 | 0 | 0 | 90 |
| 11 | 100 | 50 | — | 100 | 100 | 0 | 95 |
| 12 | 100 | 100 | — | 100 | 100 | 100 | 100 |
| 13 | 100 | 100 | — | 100 | 100 | 100 | 100 |
| 14 | 100 | 40 | — | 95 | 65 | 0 | 100 |
| 15 | 100 | 95 | — | 100 | 100 | 100 | 100 |
| 16 | 100 | — | — | 95 | 100 | 100 | 100 |
| 17 | 100 | — | 100 | 100 | 100 | 60 | 100 |
| 18 | 100 | — | 100 | 100 | 100 | 100 | 100 |
| 19 | 100 | — | 100 | 25 | 100 | 35 | 100 |
| 20 | 100 | — | 100 | 100 | 100 | 95 | 100 |
| 21 | 100 | — | 100 | 90 | 100 | 95 | 100 |
| 22 | 100 | — | 100 | 100 | 100 | 100 | 100 |
| 23 | 95 | — | 100 | 0 | 100 | — | 95 |
| 24 | 100 | — | 100 | 90 | 100 | — | 50 |
| 25 | 100 | — | 100 | 100 | 100 | — | 100 |
| 26 | 100 | — | 100 | 100 | 100 | — | 100 |
| 27 | 95 | — | 100 | 25 | 100 | — | 100 |
| 28 | 100 | — | 100 | 100 | 100 | 20 | 100 |
| 29 | 100 | — | 100 | 100 | 100 | 100 | 100 |
| 30 | 100 | — | 100 | 100 | 100 | 45 | 100 |
| 31 | 100 | — | 100 | 100 | 100 | 90 | 100 |
| 32 | 100 | — | 100 | 100 | 90 | 95 | 100 |
| 33 | 100 | — | 100 | 100 | 90 | 100 | 100 |
| 34 | 100 | — | 100 | 100 | 100 | 100 | 100 |
| 35 | 100 | — | 100 | 100 | 100 | 100 | 100 |
| 36 | 100 | — | 100 | 0 | 0 | 20 | 0 |
| 37 | 0 | — | 0 | 0 | 0 | 0 | 50 |
| 38 | 100 | — | 100 | 95 | 100 | 40 | 75 |
| 39 | 100 | — | 100 | 100 | 100 | 100 | 100 |
| 40 | 100 | — | 100 | 100 | 100 | 60 | 100 |
| 41 | 100 | — | 100 | 100 | 100 | 100 | 100 |
| 42 | 100 | — | 100 | 95 | 100 | 90 | 100 |
| 43 | 100 | — | 100 | 100 | 100 | 100 | 100 |
| 44 | 100 | — | 100 | 100 | 100 | 100 | 100 |
| 45 | 100 | — | 100 | 100 | 100 | 100 | 100 |
| 46 | 100 | — | 100 | 100 | 100 | 100 | 100 |
| 47 | 100 | — | 100 | 100 | 100 | 100 | 100 |
| 48 | 100 | — | 100 | 100 | 100 | 100 | 100 |
| 49 | 100 | — | 100 | 100 | 100 | 100 | 100 |
| 50 | 100 | — | 100 | 0 | 100 | 0 | 95 |
| 51 | 0 | — | 0 | 80 | 20 | 50 | 95 |
| 52 | 100 | — | 100 | 100 | 100 | 100 | 100 |
| 53 | 100 | — | 100 | 95 | 100 | 100 | 100 |
| 54 | 100 | — | 100 | 100 | 100 | 100 | 100 |
| 55 | 100 | — | 100 | 100 | 100 | 100 | 100 |
| 56 | 100 | — | 100 | 100 | 100 | 100 | 100 |
| 57 | 100 | — | 100 | 100 | 100 | 95 | 100 |
| 58 | 100 | — | 100 | 100 | 100 | 100 | 100 |
| 59 | 85 | — | 100 | 100 | 100 | 0 | 100 |
| 60 | 100 | — | 100 | 100 | 100 | 0 | 100 |
| 61 | 0 | — | 0 | 0 | 0 | 0 | 0 |
| 62 | 0 | — | 100 | 0 | 0 | 60 | 100 |
| 63 | 0 | — | 0 | 0 | 100 | 0 | 50 |
| 64 | 90 | — | 100 | 100 | 95 | 90 | 100 |
| 65 | 0 | — | 0 | 0 | 0 | 0 | 50 |
| 66 | 100 | — | 100 | 100 | 100 | 100 | 100 |
| 67 | 100 | — | 100 | 100 | 100 | 100 | 100 |
| 68 | 100 | — | 100 | 100 | 100 | 100 | 100 |
| 69 | 100 | — | 100 | 80 | 100 | 80 | 100 |
| 70 | 100 | — | 100 | 100 | 100 | 100 | 100 |
| 71 | 100 | — | 100 | 100 | 100 | 100 | 100 |
| 72 | 100 | — | 100 | 100 | 100 | 100 | 100 |
| 73 | 100 | — | 100 | 90 | 100 | 100 | 100 |
| 74 | 100 | — | 100 | 100 | 100 | 100 | 100 |
| 75 | 100 | — | 100 | 100 | 100 | 100 | 100 |
| 76 | 100 | — | 100 | 100 | 100 | 100 | 100 |
| 77 | 100 | — | 100 | 100 | 100 | 100 | 100 |
| 78 | 100 | 100 | 100 | 100 | 100 | 100 | 100 |
| 79 | 100 | 100 | 100 | 100 | 100 | 100 | 100 |
| 80 | 100 | 100 | 100 | 100 | 90 | 100 | 100 |
| 81 | 100 | 100 | 100 | 100 | 100 | 100 | 100 |
| 82 | 100 | 100 | 100 | 100 | 90 | 90 | 95 | 100 |
| 83 | 100 | 100 | 100 | 100 | 100 | 100 | 100 |
| 84 | 100 | 100 | 100 | 100 | 100 | 100 | 100 |
| 85 | 100 | 100 | 100 | 100 | 100 | 100 | 100 |

VI. Postemergence Control

To test the effectiveness of the compounds of this invention as postemergence herbicides, the 3000 ppm solution described in Example V (Preemergence Control) was atomized employing a DeVILBISS ™ sprayer, wetting the foliage to the drip point. The remainder of the procedure was the same as described in Example 4. The weeds, which were the same species as described in Example V, were treated six days after emergence. The percent weed control was evaluated two weeks after treatment. The results of such testing are summarized in Table III.

TABLE III

Postemergence Herbicide Activity of 3000 ppm
Percent Weed Control at 11.2 kg/ha

| Compound # | VL | JW | PS | TM | SG | BG | GF |
|---|---|---|---|---|---|---|---|
| 1 | 75 | 15 | — | 50 | 0 | 10 | 5 |
| 2 | 100 | 100 | — | 95 | 75 | 90 | 80 |
| 3 | 100 | 100 | — | 100 | 100 | 100 | 100 |
| 4 | 20 | 0 | — | 30 | 20 | 75 | 65 |
| 5 | 15 | 10 | — | 15 | 0 | 5 | 0 |
| 6 | 100 | 100 | — | 100 | 45 | 80 | 95 |
| 7 | 100 | 100 | — | 100 | 20 | 55 | 50 |
| 8 | 0 | 0 | — | 0 | 0 | 0 | 0 |
| 9 | 0 | 0 | — | 0 | 0 | 0 | 0 |
| 10 | 50 | 30 | — | 55 | 0 | 5 | 5 |
| 11 | 95 | 95 | — | 100 | 0 | 25 | 10 |
| 12 | 100 | 100 | — | 100 | 25 | 60 | 45 |
| 13 | 100 | 95 | — | 100 | 10 | 70 | 55 |
| 14 | 80 | 50 | — | 70 | 35 | 0 | 25 |
| 15 | 95 | 50 | — | 95 | 5 | 5 | 10 |
| 16 | 100 | 100 | — | 100 | 100 | 100 | 100 |
| 17 | 100 | — | — | 100 | 75 | 80 | 95 |
| 18 | 100 | — | — | 90 | 100 | 90 | 100 |
| 19 | 95 | — | — | 40 | 30 | 45 | 35 |
| 20 | 100 | — | 80 | 100 | 70 | 65 | 45 |
| 21 | 100 | — | 90 | 100 | 95 | 85 | 85 |
| 22 | 100 | — | 100 | 100 | 95 | 70 | 85 |
| 23 | 100 | — | 100 | 100 | 75 | 100 | 85 |
| 24 | 100 | — | 90 | 100 | 80 | 80 | 45 |
| 25 | 100 | — | 100 | 100 | 40 | 75 | 45 |
| 26 | 100 | — | 95 | 100 | 40 | 75 | 65 |
| 27 | 100 | — | 90 | 100 | 35 | 60 | 20 |
| 28 | 100 | — | 100 | 75 | 50 | 85 | 20 |

TABLE III-continued

Postemergence Herbicide Activity of 3000 ppm
Percent Weed Control at 11.2 kg/ha

| Compound # | VL | JW | PS | TM | SG | BG | GF |
|---|---|---|---|---|---|---|---|
| 29 | 100 | — | 100 | 100 | 10 | 75 | 55 |
| 30 | 100 | — | 100 | 100 | 15 | 40 | 25 |
| 31 | 100 | — | 100 | 85 | 30 | 70 | 15 |
| 32 | 100 | — | 100 | 70 | 60 | 75 | 100 |
| 33 | 100 | — | 100 | 95 | 95 | 80 | 100 |
| 34 | 100 | — | 95 | 100 | 30 | 40 | 95 |
| 35 | 100 | — | 100 | 100 | 75 | 80 | 50 |
| 36 | 100 | — | 30 | 15 | 5 | 20 | 25 |
| 37 | 65 | — | 40 | 10 | 0 | 15 | 20 |
| 38 | 100 | — | 100 | 95 | 20 | 45 | 15 |
| 39 | 100 | — | 100 | 100 | 100 | 100 | 100 |
| 40 | 100 | — | 100 | 100 | 90 | 35 | 80 |
| 41 | 100 | — | 100 | 100 | 100 | 95 | 90 |
| 42 | 100 | — | 100 | 60 | 40 | 50 | 30 |
| 43 | 100 | — | 100 | 100 | 100 | 90 | 85 |
| 44 | 100 | — | 100 | 95 | 55 | 70 | 45 |
| 45 | 100 | — | 100 | 90 | 10 | 45 | 55 |
| 46 | 100 | — | 100 | 100 | 5 | 70 | 95 |
| 47 | 95 | — | 95 | 90 | 10 | 15 | 100 |
| 48 | 100 | — | 100 | 100 | 100 | 90 | 100 |
| 49 | 100 | — | 100 | 100 | 100 | 75 | 100 |
| 50 | 95 | — | 90 | 40 | 0 | 0 | 0 |
| 51 | 100 | — | 100 | 95 | 10 | 30 | 20 |
| 52 | 100 | — | 100 | 100 | 100 | 50 | 100 |
| 53 | 100 | — | 100 | 100 | 100 | 95 | 100 |
| 54 | 100 | — | 100 | 100 | 100 | 100 | 100 |
| 55 | 100 | — | 100 | 95 | 20 | 90 | 65 |
| 56 | 100 | — | 100 | 100 | 100 | 100 | 100 |
| 57 | 100 | — | 100 | 100 | 100 | 60 | 70 |
| 58 | 100 | — | 100 | 100 | 100 | 100 | 95 |
| 59 | 95 | — | 95 | 65 | 0 | 0 | 0 |
| 60 | 100 | — | 100 | 100 | 95 | 95 | 90 |
| 61 | 15 | — | 0 | 0 | 0 | 0 | 0 |
| 62 | 15 | — | 10 | 20 | 0 | 0 | 0 |
| 63 | 10 | — | 5 | 10 | 15 | 0 | 0 |
| 64 | 25 | — | 50 | 10 | 10 | 0 | 75 |
| 65 | 0 | — | 0 | 0 | 0 | 0 | 0 |
| 66 | 100 | — | 100 | 100 | 90 | 75 | 85 |
| 67 | 100 | — | 100 | 100 | 100 | 100 | 100 |
| 68 | 100 | — | 100 | 100 | 100 | 95 | 100 |
| 69 | 100 | — | 100 | 100 | 85 | 65 | 80 |
| 70 | 100 | — | 100 | 100 | 90 | 90 | 95 |
| 71 | 100 | — | 100 | 100 | 100 | 100 | 100 |
| 72 | 100 | — | 100 | 100 | 100 | 100 | 100 |
| 73 | 100 | — | 100 | 100 | 100 | 100 | 100 |
| 74 | 100 | — | 100 | 100 | 90 | 75 | 95 |
| 75 | 100 | — | 100 | 100 | 100 | 100 | 100 |
| 76 | 100 | — | 100 | 100 | 100 | 95 | 100 |
| 77 | 100 | — | 100 | 100 | 100 | 100 | 100 |
| 78 | 100 | 100 | 100 | 100 | 100 | 100 | 95 |
| 79 | 100 | 100 | 100 | 100 | 100 | 100 | 100 |
| 80 | 100 | 100 | 100 | 100 | 80 | 70 | 80 |
| 81 | 100 | 100 | 100 | 100 | 65 | 95 | 90 |
| 82 | 100 | 100 | 100 | 60 | 20 | 35 | 15 |
| 83 | 100 | 100 | 100 | 100 | 100 | 100 | 90 |
| 84 | 100 | 100 | 100 | 100 | 100 | 100 | 100 |
| 85 | 100 | 100 | 100 | 100 | 100 | 90 | 65 |

What is claimed is:

1. A compound of the structural formula

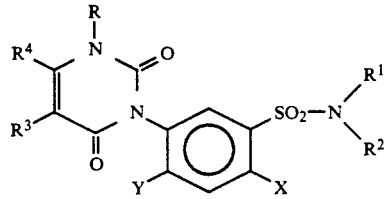

wherein

R is hydrogen, $C_1$-$C_4$ alkyl, $C_1$-$C_4$ haloalkyl, formyl, $C_2$-$C_6$ alkanoyl, $C_3$-$C_4$ alkenyl or $C_3$-$C_4$ alkynyl, or alkali metal;

X is $C_1$-$C_4$ alkyl, $C_1$-$C_8$ alkoxy, cyano, or halogen;

Y is hydrogen, halogen, or $C_1$-$C_4$ dialkylamino;

$R^1$ is hydrogen, $C_1$-$C_8$ straight chain or branched alkyl, $C_3$-$C_8$ cycloalkyl, $C_3$-$C_8$ alkenyl, $C_3$-$C_8$ alkoxy or $C_3$-$C_8$ hydroxyalkyl;

$R^2$ is hydrogen, $C_1$-$C_8$ straight chain or branched alkyl, $C_3$-$C_8$ alkenyl, $C_3$-$C_8$ cycloalkyl, halo substituted $C_3$-$C_8$ alkenyl, $C_3$-$C_8$ alkynyl, $C_1$-$C_4$ alkoxy, hydroxy $C_1$-$C_4$ alkyl, cyano $C_1$-$C_4$ alkyl, 2,3-epoxypropyl, 2,2-dialkoxyethyl, $C_2$-$C_5$ alkoxyalkyl, phenyl, benzyl, $C_1$-$C_4$ acyl, $C_1$-$C_4$ carbalkoxyalkyl, $C_1$-$C_4$ carbalkoxyalkyl substituted by $C_1$-$C_4$ alkyl, phenylmethyl or methylthioethyl, (1,3-dioxolan-2-yl) $C_1$-$C_4$ alkyl, diethylaminoethyl, or tetrahydrofuranylmethyl; or $R^1$ and $R^2$ taken together form a $C_3$-$C_8$ membered heterocyclic ring containing one or two heteroatoms;

$R^3$ is hydrogen, halogen or $C_1$-$C_4$ alkyl; and $R^4$ is $C_1$-$C_4$ alkyl or $C_1$-$C_4$ haloalkyl.

2. A compound in accordance with claim 1 wherein R is $C_1$-$C_3$ alkyl or $C_3$-$C_4$ alkynyl; X is halogen or $C_1$-$C_3$ alkyl; Y is halogen or hydrogen; $R^1$ is hydrogen, $C_1$-$C_3$ alkyl or hydroxy $C_3$-$C_8$ alkyl; $R^2$ is $C_1$-$C_3$ alkyl, $C_3$-$C_8$ cycloalkyl, $C_3$-$C_4$ alkenyl, $C_3$-$C_5$ alkoxyalkyl, hydroxy $C_1$-$C_4$ alkyl or 2,3 epoxypropyl; $R^3$ is hydrogen; and $R^4$ is $C_1$-$C_4$ haloalkyl.

3. A compound in accordance with claim 1 wherein R is methyl; X is chlorine or fluorine; Y is fluorine or hydrogen; $R^1$ is hydrogen, methyl, or hydroxy $C_1$-$C_4$ alkyl; $R^2$ is hydrogen, $C_1$-$C_4$ alkyl, $C_3$-$C_6$ cycloalkyl, $C_1$-$C_4$ alkoxy, alkoxyalkyl, hydroxy $C_1$-$C_4$ alkyl, cyanoalkyl, 2,2 dialkoxyethyl, or carbalkoxyalkyl; $R^3$ is hydrogen; and $R^4$ is trifluoromethyl.

4. A compound in accordance with claim 1 wherein R is methyl; X is chlorine; Y is hydrogen or fluorine; $R^1$ is methyl, ethyl, or hydrogen; $R^2$ is methyl, ethyl, methoxy, hydroxyethyl, acetyl, methoxyethyl, 2,2 dimethoxyethyl, 1-carbethoxyethyl, or 1-carbethoxy-2-methylpropyl; $R^3$ is hydrogen; and $R^4$ is trifluoromethyl.

5. A herbicidal composition comprising an effective amount of at least one of the compounds of claim 1 and a suitable carrier therefor.

6. A herbicidal composition comprising an effective amount of at least one of the compounds of claim 2 and a suitable carrier therefor.

7. A herbicidal composition comprising an effective amount of at least one of the compounds of claim 3 and a suitable carrier therefor.

8. A herbicidal composition comprising an effective amount of at least one of the compounds of claim 4 and a suitable carrier therefor.

9. A method for controlling weeds comprising applying a herbicidally effective amount of a composition according to claim 5 to weeds and/or to the locus to be protected against weeds.

10. A method for controlling weeds comprising applying a herbicidally effective amount of a composition according to claim 6 to weeds and/or to the locus to be protected against weeds.

11. A method for controlling weeds comprising applying a herbicidally effective amount of a composition according to claim 7 to weeds and/or to the locus to be protected against weeds.

12. A method for controlling weeds comprising applying a herbicidally effective amount of a composition according to claim 4 to weeds and/or to the locus to be protected against weeds.